(12) United States Patent
Yeung et al.

(10) Patent No.: US 10,548,854 B2
(45) Date of Patent: Feb. 4, 2020

(54) MANUFACTURE OF NONELECTRONIC, ACTIVE-INFUSION PATCH AND DEVICE FOR TRANSDERMAL DELIVERY ACROSS SKIN

(71) Applicant: The Hong Kong University of Science and Technology, Hong Kong (CN)

(72) Inventors: King Lun Yeung, Hong Kong (CN); Wai Kit Wong, Hong Kong (CN); Siu Ming Kwan, Hong Kong (CN); Li Yin Chau, Hong Kong (CN); Ho Yee Timothy Poon, Hong Kong (CN); Ming Hung Thomas Lee, Hong Kong (CN); Albert Hee Lum Chow, Hong Kong (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 368 days.

(21) Appl. No.: 14/432,634

(22) PCT Filed: Sep. 23, 2013

(86) PCT No.: PCT/CN2013/001123
§ 371 (c)(1),
(2) Date: Mar. 31, 2015

(87) PCT Pub. No.: WO2014/053081
PCT Pub. Date: Apr. 10, 2014

(65) Prior Publication Data
US 2015/0238433 A1    Aug. 27, 2015

Related U.S. Application Data
(60) Provisional application No. 61/744,636, filed on Oct. 1, 2012.

(51) Int. Cl.
*A61M 37/00* (2006.01)
*A61K 9/70* (2006.01)
(Continued)

(52) U.S. Cl.
CPC .......... *A61K 9/703* (2013.01); *A61K 9/0021* (2013.01); *A61K 9/7084* (2013.01); (Continued)

(58) Field of Classification Search
CPC .... A61M 5/46; A61M 5/14248; A61M 5/158; A61M 2005/14252; A61M 2005/1586; (Continued)

(56) References Cited

U.S. PATENT DOCUMENTS 3,964,482 A     6/1976   Gerstel et al.
4,753,651 A *   6/1988   Eckenhoff ......... A61M 5/14248
                                                        424/449

(Continued)

FOREIGN PATENT DOCUMENTS

CN      1186659 A      7/1998
CN      101002756 A    7/2007

OTHER PUBLICATIONS

Zhang, J., et al., A novel two-level microstructured poly(N-isopropylacrylamide) hydrogel for controlled release, Acta Biomaterialia, 2010, 6:3890-3898, 2010 Acta Materialia Inc., Elsevier Ltd.
(Continued)

*Primary Examiner* — Imani N Hayman
*Assistant Examiner* — Tezita Z Watts
(74) *Attorney, Agent, or Firm* — Saliwanchik, Lloyd & Eisenschenk

(57) ABSTRACT

Transdermal patches and devices for delivery of therapeutic drug and/or cosmetic formulations through an intact or porated skin barrier are described. Active-infusion delivers controlled dosing over a period of time to provide long-term
(Continued)

efficacy. Methods and devices for preparing active-infusion patches for controlled dose delivery by nonelectronic devices and methods of skin poration that is safe and painless are described.

19 Claims, 22 Drawing Sheets
(7 of 22 Drawing Sheet(s) Filed in Color)

(51) Int. Cl.
    *A61K 9/00*      (2006.01)
    *A61K 31/196*    (2006.01)
    *A61K 38/28*     (2006.01)

(52) U.S. Cl.
    CPC ............ *A61K 31/196* (2013.01); *A61K 38/28* (2013.01); *A61M 37/0015* (2013.01); *A61M 2037/0023* (2013.01)

(58) Field of Classification Search
    CPC .. A61M 2005/1426; A61M 5/28; A61M 5/42; A61M 5/142; A61M 5/14593; A61M 5/14276; A61M 5/1483; A61M 37/00; A61M 37/0015
    USPC ...................................................... 604/892.1
    See application file for complete search history.

(56) References Cited

U.S. PATENT DOCUMENTS

| | | | |
|---|---|---|---|
| 4,879,119 A | 11/1989 | Konno et al. | |
| 4,908,213 A | 3/1990 | Govil et al. | |
| 5,312,456 A | 5/1994 | Reed et al. | |
| 5,672,167 A * | 9/1997 | Athayde ............. | A61M 5/1483 604/131 |
| 5,800,420 A | 9/1998 | Gross et al. | |
| 6,334,856 B1 | 1/2002 | Allen et al. | |
| 6,451,240 B1 | 9/2002 | Sherman et al. | |
| 6,844,213 B2 | 1/2005 | Sparks | |
| 6,924,087 B2 | 8/2005 | Yeshurun et al. | |
| 7,097,776 B2 | 8/2006 | Govinda Raju | |
| 7,332,339 B2 | 2/2008 | Canham | |
| 7,497,980 B2 | 3/2009 | Xu et al. | |
| 7,588,552 B2 | 9/2009 | Yeshurun et al. | |
| 7,699,819 B2 | 4/2010 | Yeung et al. | |
| 7,798,987 B2 | 9/2010 | Trautman et al. | |
| 8,043,250 B2 | 10/2011 | Xu | |
| 8,062,835 B2 | 11/2011 | Tomono | |
| 8,137,736 B2 | 3/2012 | Zhu et al. | |
| 8,150,505 B2 | 4/2012 | Herndon | |
| 8,162,901 B2 | 4/2012 | Gonnelli et al. | |
| 8,197,435 B2 | 6/2012 | Prausnitz et al. | |
| 2006/0055090 A1 | 3/2006 | Lee et al. | |
| 2007/0225676 A1 | 9/2007 | Prausnitz et al. | |
| 2009/0030365 A1 | 1/2009 | Tokumoto et al. | |
| 2009/0099502 A1 | 4/2009 | Tokumoto et al. | |
| 2011/0172639 A1 * | 7/2011 | Moga ................. | A61M 5/14224 604/506 |
| 2011/0237925 A1 | 9/2011 | Yue et al. | |
| 2011/0288485 A1 | 11/2011 | Tokumoto et al. | |

OTHER PUBLICATIONS

Zhao, J. et al., A novel transdermal patch incorporating isosorbide dinitrate with bisoprolol: In vitro and in vivo characterization, International Journal of Pharmaceutics, 2007, 337:88-101, 2007 Elsevier B.V.

Kumar, A., et al., Development of PEGDMA: MAA based hydrogel microparticles for oral insulin delivery, International Journal of Pharmaceutics, 2006, 323:117-124, 2006 Elsevier B.V.

Varghese, E., et al., Enhanced skin permeation of diclofenac by iontophoresis: in vitro and in vivo studies, Journal of Controlled Release, 1996, 38:21-27, 1996 Elsevier Science B.V.

Yan, G., et al., Evaluation needle length and density of microneedle arrays in the pretreatment of skin for transdermal drug delivery, International Journal of Pharmaceutics, 2010, 391:7-12, 2010 Elsevier B.V.

Deligkaris, K., et al., Hydrogel-based devices for biomedical applications, Sensors and Actuators B: Chemical, 2010, 147:765-774, 2010 Elsevier B.V.

Caykara, T., et al., Macroporous Poly(Acrylamide) Hydrogels: Swelling and Shrinking Behaviors, *Journal of Macromolecular Science®, Part A: Pure and Applied Chemistry*, 2006, 43:889-897, Taylor & Francis Group, LLC.

Gu, J., et al., Programmable delivery of hydrophilic drug using dually responsive hydrogel cages, Journal of Controlled Release, 2007, 117:396-402, 2006 Elsevier B.V.

Yung, K. L., et al., Sharp tipped plastic hollow microneedle array by microinjection moulding, Journal of Micromechanics and Microengineering, 2012, vol. 22, No. 1, 11 pages, 2012 IOP Publishing Ltd.

International Search Report in International Application No. PCT/CN2013/001123, filed Sep. 23, 2013.

Prausnitz, Mark R. et al., Current Status and Future Potential of Transdermal Drug Delivery, Nature Reviews Drug Discovery, Feb. 2004, 3(2):115-124, www.nature.com/reviews/drugdisc.

Plapied, Laurence et al., Fate of polymeric nanocarriers for oral drug delivery, Current Opinion in Colloid & Interface Science, Jun. 2011, 16(3):228-237, Elsevier Ltd.

Gordon, Ryan D., Dr. et al., 4 Myths About Transdermal Drug Delivery, Drug Development & Delivery, Jun. 2003, 3(4):1-15, Drug Development & Delivery.

Srodin, Sharon, Transdermal Drug Delivery—Innovations in Technologies Are Opening Market Opportunities, Ezine Articles, Jul. 27, 2007, Ezine Articles, http://EzineArticles.com/expert/Sharon_Srodin/112771.

Stockwell, K.A. et al., Continuous delivery of ropinirole reverses motor deficits without dyskinesia induction in MPTP-treated common marmosets, Experimental Neurology, May 2008, 211(1):172-179, Elsevier Inc.

Sloan, Paul A. et al., A Clinical Evaluation of Transdermal Therapeutic System Fentanyl for the Treatment of Cancer Pain, Journal of Pain and Symptom Management, Aug. 2, 1998, 16(2):102-111, Elsevier.

Hemkens, L.G. et al., Risk of malignancies in patients with diabetes treated with human insulin or insulin analogues: a cohort study, Diabetologia, 2009, 52(9):1732-1744, Springer.

Glenn, G.M. et al., Mass Vaccination: Solutions in the Skin, Current Topics in Microbiology and Immunology, 2006, 304:247-268, Springer-Verlag Berlin Heidelberg.

Prausnitz, Mark R. et al., Transdermal drug delivery, Nature Biotechnology, Nov. 2008, 26(11):1261-1268, Nature Publishing Group.

Sivamani, Raja K. et al., Clinical microneedle injection of methyl nicotinate: stratum corneum penetration, Skin Research and Technology, 2005, 11(2):152-156, Blackwell Munksgaard.

McAllister, Devin V. et al., Microfabricated needles for transdermal delivery of macromolecules and nanoparticles: Fabrication methods and transport studies, Proceedings of the National Academy of Sciences of the United States of America (PNAS), Nov. 25, 2003, 100(24):13755-13760, PNAS.

Roxhed, Niclas et a., Painless Drug Delivery Through Microneedle-Based Transdermal Patches Featuring Active Infusion, IEEE Transactions on Biomedical Engineering, Mar. 2008, 55(3):1063-1071, IEEE.

Richter, Andreas et al., Adjustable Low Dynamic Pumps Based on Hydrogels, Macromolecular Symposia, Mar. 2004, 210(1):377-384, Wiley-VCH, Germany.

\* cited by examiner

MANUFACTURE OF NONELECTRONIC, ACTIVE-INFUSION PATCH AND DEVICE FOR TRANSDERMAL DELIVERY ACROSS SKIN

CROSS-REFERENCE TO RELATED APPLICATIONS

This application is the U.S. national stage application of International Patent Application No. PCT/CN2013/001123, filed Sep. 23, 2013, which claims priority to U.S. Provisional Application No. 61/744,636, filed Oct. 1, 2012, the disclosures of each of which are incorporated herein by reference in their entirety.

FIELD OF THE INVENTION

The present invention pertains to embodiments for the design and manufacture of active-infusion patch devices. Embodiments of the invention can include an actuating device and a volume of therapeutic drug and/or cosmetic formulation disposed within separate compartments that are connected through a membrane. One embodiment of the actuating device includes an expanding hydrogel that can expand at a constant or a fixed rate to deliver a constant dosing rate of the therapeutic drug and/or cosmetic formulation. In a further embodiment, the patch device can be operatively connected to at least one microneedle or a microneedle plate for skin poration to enhance delivery across skin.

BACKGROUND OF THE INVENTION

The most common routes for drug delivery are by oral administration, hypodermic injection, and transdermal delivery. Transdermal delivery is usually painless when compared to hypodermic injection and does not generate dangerous medical waste or pose a risk of disease transmission from needle reuse, which is common in developing countries (Prausnitz et al., 2004). Transdermal delivery also has some advantages over oral routes, which often have poor drug absorption or results in enzymatic degradation in the gastrointestinal tract or liver (Plapied et al., 2011). Transdermal drug delivery devices are typically noninvasive/minimally invasive, can be self-administered, and result in a high degree of patient compliance. They can also provide an inexpensive drug delivery system with capacity for long-term controlled release.

The United States Food and Drug Administration (USFDA) approved the first transdermal patch in 1981 for scopolamine, a drug that suppresses nausea and vomiting from motion sickness (Gorden et al., 2003). In the United States market, more than 35 transdermal products were introduced during the last two decades, generating total sales of USD 5.7 billion in 2006 (Srodin, 2007). The market is expected to continue to increase as the use transdermal delivery devices are utilized with more substances.

Recently, the advantage of continuous drug delivery has drawn considerable attention over conventional short-term single dose delivery devices, such as those described in U.S. Published application nos. 2007/0225676, 2009/0099502, 2009/0030365, and 2011/0288485. In fact, much research has been done indicating that there are some advantages to continuous drug delivery. For example, research has shown that dyskinesia levels, a motor complication of Parkinson's disease patients, when treated with continuous subcutaneous delivery of ropinrole was lower than that of patients having twice daily oral administration (Stockwell et al., 2008). Clinical studies have also shown that 63% of cancer patients preferred the use of transdermal delivery of fentanyl administrated every 3 days over chronic oral morphine analgesia in pain killing (Sloan et al., 1998). For patients suffering from diabetes mellitus, continuous delivery of human insulin (short acting/regular) could be better than single dose delivery of insulin analogues (long acting), as studies have revealed that the injection of insulin analogues may lead to unexpected outcome (Hemkens et al., 2009). In short, continuous drug delivery has offered some advantages over single dose/bolus therapy in different biomedical applications. Designing a continuous delivery patch that can be loaded with one or more of a variety of drugs and/or analgesics gives rise to a large market potential and greater patient convenience.

Conventional transdermal patches consist of three main components: a backing membrane preventing the drug from dehydration and contamination; a drug reservoir for drug storage therein; and a permeable membrane, directed towards and/or in contact with the skin, that controls the drug diffusion rate across skin. The permeable membrane of the patch can usually be adhered to the skin. The effectiveness of transdermal delivery is usually limited by drug permeability across the lipoidal barrier of the stratum corneum. Drugs that are presently administered across the skin often share three constraining characteristics: low molecular mass (<500 Da), high lipophilicity (oil soluble), and small required dosage (i.e., usually only up to milligram amounts). Opening the transdermal delivery route for large hydrophilic drugs and vaccines is a major challenge, but one that, if overcome, will revolutionize healthcare and medicinal practices. The transdermal delivery of vaccines can avoid not only the use of hypodermic needles (Clenn et al., 2006), but has the potential to improve immune response by targeting the delivery to immunogenic Langerhans cells in skin (Prausnitz et al., 2008).

Most of the transdermal systems currently used are coupled with passive infusion (i.e., drug delivery through a barrier by diffusion), which may not be applicable when significant and precise amounts of drug release are required. Active infusion, a method of drug delivery by forcing a drug-containing liquid into tissues by mechanical means, is thereby a preferred solution. Indeed, studies have shown active infusion with micro-needles is a feasible method for drug delivery (Sivamani et al., 2005). McAllister et al. has demonstrated the use of micro-needles and pressure force (10 psi) to lower 70% of the normalized blood glucose level by insulin delivered in vivo (McAllister et al., 2003). Regulated drug delivery devices were employed by Roxhed et al. with the device having a printed circuit board and Richter et al. used an autonomous pump (Roxhed et al., 2008 and Richter et al., 2004). However, the involvement of the use of battery power hampers the portable usage of the device of Roxhed's design and the pump of Richter's device is probably too bulky to be portable for daily use. The ability to easily sterilize the drug ampoule or other reservoir in patch devices is yet another concern.

The development of a small, disposable, and safe transdermal patch with long-term and consistent or steady drug delivery is therefore highly desirable. The embodiments of the subject invention address these issues in an advantageous design that can be easily manufactured and employed with a variety of substances.

BRIEF SUMMARY OF THE INVENTION

The present invention describes transdermal patches and related devices for delivery of therapeutic drugs and/or cosmetic formulations across a skin barrier at a controlled rate by a nonelectronic means. The patch device can utilize a non-electronic actuating device and a volume of therapeutic drug and/or cosmetic formulation, which can be disposed in separate compartments that are connected by a membrane. In a specific embodiment, the actuating device utilizes an expanding hydrogel that expands at a constant rate to deliver a constant rate and/or fixed amount of a therapeutic drug and/or cosmetic formulation. The patch device can be further attached to at least one microneedle or microneedle plate for skin poration to enhance delivery across skin.

BRIEF DESCRIPTION OF DRAWINGS

The patent or application file contains at least one drawing executed in color. Copies of this patent or patent application publication with color drawing(s) will be provided by the Office upon request and payment of the necessary fee.

In order that a more precise understanding of the above recited invention can be obtained, a more particular description of the invention briefly described above will be rendered by reference to specific embodiments thereof that are illustrated in the appended drawings. The drawings presented herein may not be drawn to scale and any reference to dimensions in the drawings or the following descriptions are specific to the embodiments disclosed. Any variations of these dimensions that will allow the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings in which:

FIG. 1A is a top plan view that illustrates one embodiment of the structures of the drug reservoir and FIG. 1B is a top plan view that illustrates one embodiment of the water and hydrogel reservoirs formed as part of the body piece. FIG. 1C is a cross-sectional view taken along line A-A' in FIG. 1A, and FIG. 1D is a cross-sectional view taken along line B-B' in FIG. 1B showing details of certain features.

FIGS. 2A, 2B, 2C, and 2D illustrate another embodiment of a patch device of the subject invention, wherein FIG. 2A is a top plan view showing the water and hydrogel reservoirs of the device and FIG. 2B is a top plan view showing a turnable break gate cover. FIG. 1C is a cross-sectional view taken along line C-C' in FIG. 2A, and FIG. 2D is a cross-sectional view taken along line D-D' in FIG. 2B.

FIGS. 3A, 3B, 3C, and 3D illustrate yet another embodiment of a patch device of the subject invention, wherein FIG. 3A is a top plan view showing the structures of the water and hydrogel reservoirs of the device and FIG. 3B is a top plan view showing the switch cover. FIG. 3C is a cross-sectional view taken along line E-E' in FIG. 3A, and FIG. 3D is a cross-sectional view taken along line F-F' in FIG. 3D.

FIG. 13A shows the device when gates are closed and FIG. 13B shows the device with the gates opened. FIG. 13C shows the embodiment assembled with the key unattached.

FIG. 21A illustrates an embodiment of a wearable patch housing and FIG. 21B is a photograph showing an embodiment of a complete wearable transdermal device prototype.

DETAILED DISCLOSURE

Figure 1A:
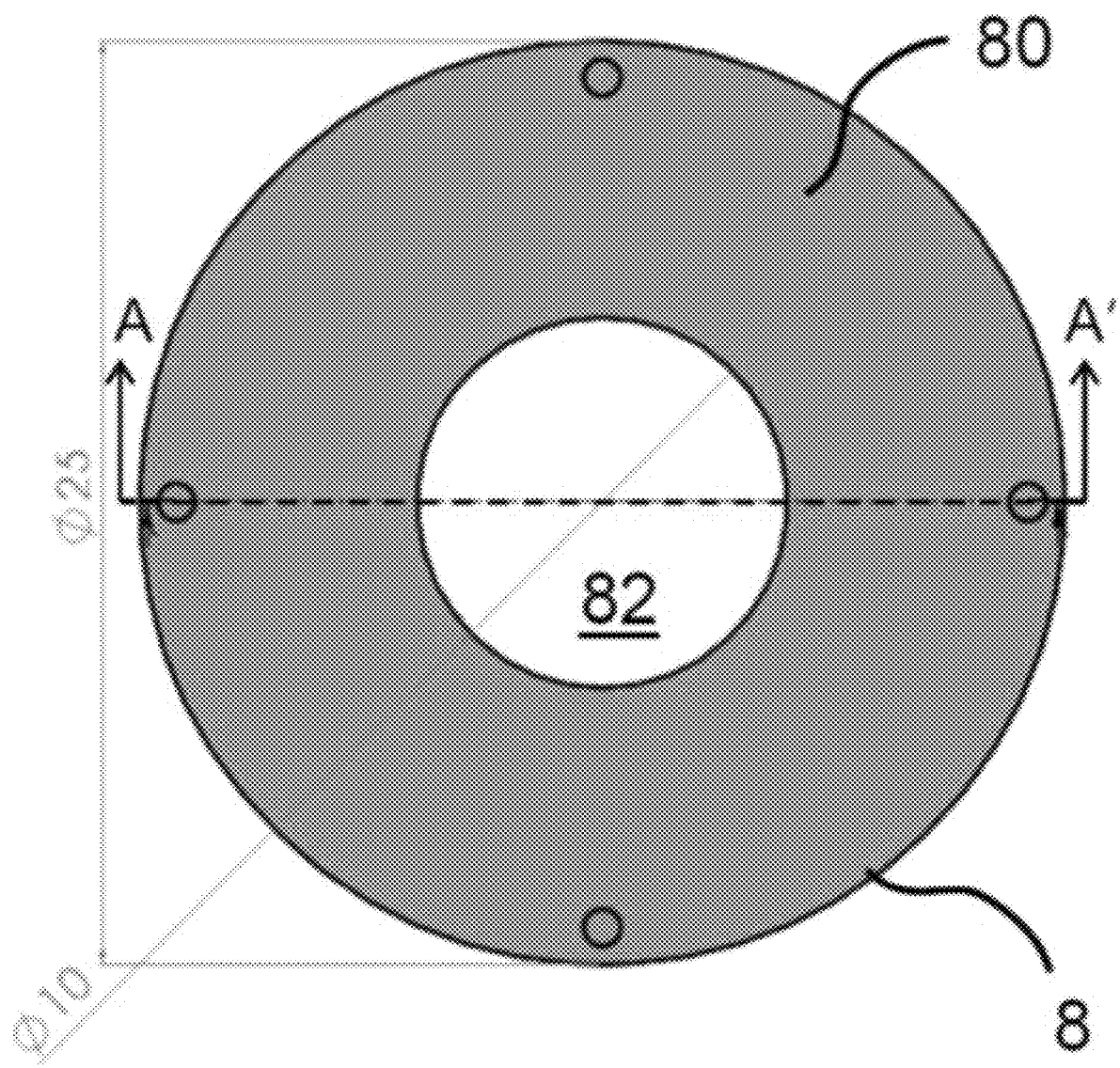
FIGS. 1A, 1B, 1C, and 1D illustrate one embodiment of a patch device of the subject invention, where

The subject invention pertains, in general, to patches with transmission-capable barriers. More specifically, the subject invention provides embodiments of transdermal patches, or similar devices, capable of providing long-term sustained release of a substance. Particular embodiments of the invention provide a mechanism by which the device can be activated and allows control of the amount of substance released.

The following description will disclose that the subject invention is particularly useful in the field of drug delivery, in particular devices used for the transdermal delivery of substances. However, a person with skill in the art will be able to recognize numerous other uses that would be applicable to the devices and methods of the subject invention. While the subject application describes, and many of the terms herein relate to, a use for transdermal delivery of a sustained release substance, other modifications and uses that are apparent to a person with skill in the art having benefit of the subject disclosure are contemplated to be within the scope of the present invention.

In the description that follows, a number of terms used in relation to methods and devices for substance release and transmission are utilized. In order to provide a clear and consistent understanding of the specification and claims, including the scope to be given such terms, the following definitions are provided.

The term "patient" as used herein, describes an invertebrate or vertebrate animal, including mammals to which the systems and methods of the present invention are applied. Mammalian species that can benefit from the disclosed systems and methods include, but are not limited to, apes, chimpanzees, orangutans, humans, monkeys, whales, dolphins; domesticated animals (e.g., pets) such as dogs, cats, guinea pigs, hamsters, rabbits; veterinary uses for large animals such as cattle, horses, goats, sheep; and any wild animal for veterinary or tracking purposes. Human or non-human animal patients can range in age from neonates to elderly.

Also, as used herein, and unless otherwise specifically stated, the terms "operably communicate," "operable connection," "operably connected," and literary variations thereof mean that the particular elements are connected in such a way that they cooperate to achieve their intended function or functions. The "communication" or "connection" may be direct, or indirect, physical, or remote.

The term "drug" as used herein refers to any substance that can be administered transdermally by the devices of the subject invention. This can include, but is not limited to, chemicals, pharmaceuticals, supplements, vitamins, hormones, lipids, polypeptides, vaccines, anti-inflammatories, opiates, serums, or any substance used for diagnostic, therapeutic, prophylactic, or cosmetic purposes, etc.

Finally, reference is made throughout the application to the "proximal side" and "distal side." As used herein, the proximal side is that side that is closest to the skin when the device is attached to a patient. Conversely, the distal side of the device is that side located furthest from the skin when the device is attached to a patient.

The present invention is more particularly described in the following examples that are intended to be illustrative only since numerous modifications and variations therein will be apparent to those skilled in the art. As used in the specification and in the claims, the singular for "a," "an" and "the" include plural referents unless the context clearly dictates otherwise.

Reference will be made to the attached figures on which the same reference numerals are used throughout to indicate the same or similar components. With reference to the attached figures, which show certain embodiments, it can be seen that the subject invention comprises a compartmentalized container in the form of a wearable patch that can be temporarily attached to or at least against the skin. In general, embodiments of a patch 10 include an actuator compartment 50 and an activator compartment 60 with a body piece overlay 80 having a drug reservoir therein that can be separated from at least the actuator compartment by a membrane 90. The actuator and activator compartments can be at least partially formed within or as part of a body piece 150 of the patch. Alternatively, the compartments can be partially configured with an insert 20 that fits into and/or against a body piece 150 to create the compartments. The activator compartment and actuator compartments can have an operable communication therebetween. In a further embodiment, the patch can optionally include one or more microneedles 100 for skin poration. In particular embodiments, the patch can be disposed within a housing 200 that can further include attachment devices 220 that make the patch wearable.

Transdermal Patches and Related Devices

Embodiments of the transdermal patches and devices of the subject invention can be manufactured by any of a variety of techniques known to those with skill in the art. By way of non-limiting examples, the patches and devices of the subject invention can be manufactured by injection moulding, hot embossing, rapid prototyping, 3-D printing, and other methods. In addition, the patches and devices of the subject invention can be manufactured using any of a variety of materials known to those with skill in the art, such as, but not limited to, acrylonitrile butadiene styrene, poly (methyl methacrylate), poly(vinyl chloride), polycarbonate, polyphenylsulfone polymer or similar polymer materials. Substitution of other manufacturing methods or materials, which achieve the same purpose, in substantially the same way, with substantially the same result are within the scope of this invention.

In one embodiment, a disposable transdermal patch is between 5 mm and approximately 30 mm in diameter. In more specific embodiment, a disposable transdermal patch of the subject invention is between approximately 5 mm and approximately 10 mm in diameter. In a further embodiment, a transdermal patch of the subject invention has a thickness, from the proximal side 5 to the distal side 15, of between approximately 1 mm and approximately 10 mm. In a more specific embodiment, a transdermal patch of the subject invention has a thickness, from the proximal side 5 to the distal side 15, of between approximately 1 mm and approximately 5 mm.

Figure 9:
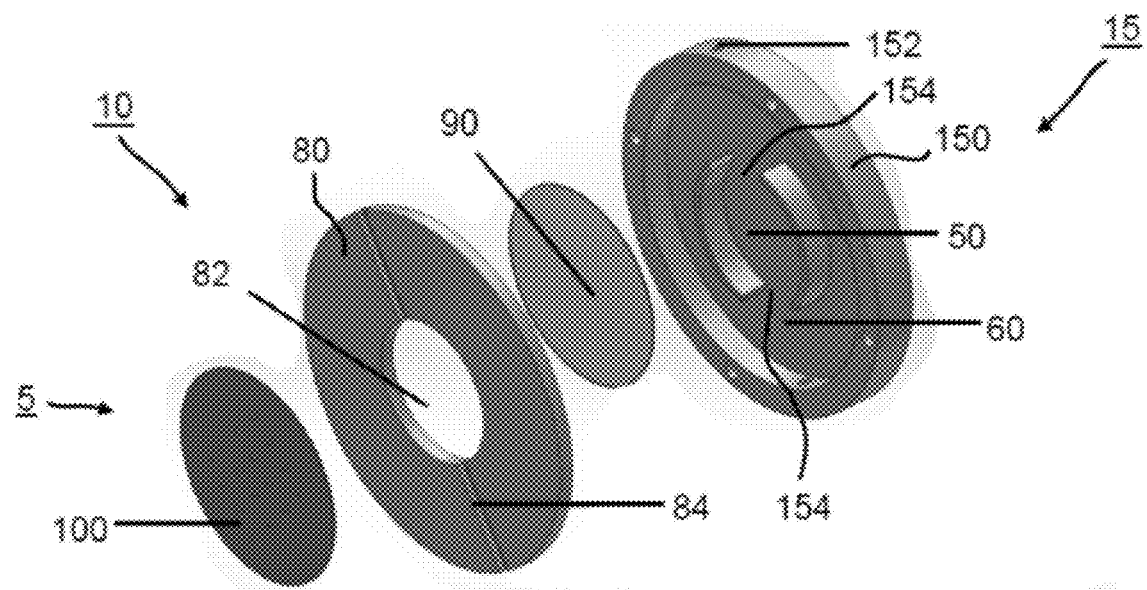
FIG. 9 is an exploded view of one embodiment of an active infusion transdermal microneedle patch, according to the subject invention. In this embodiment, part of the activator compartment and actuator compartment are formed directly into the body piece.
Figure 10:
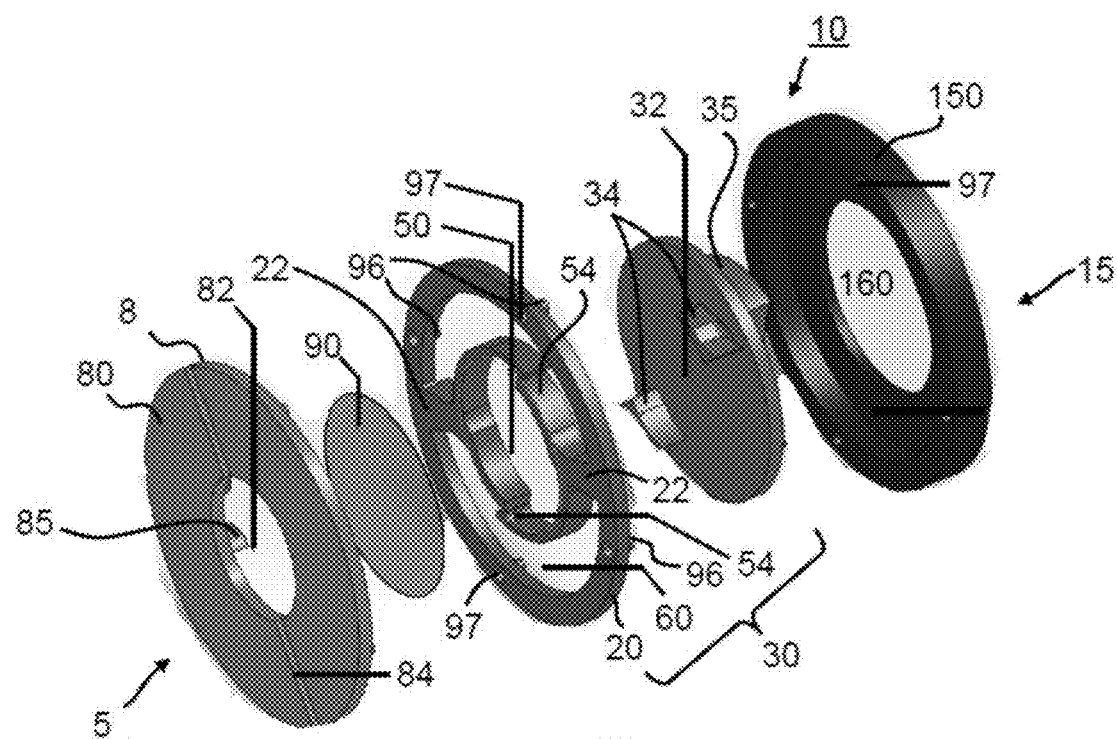
FIG. 10 is an exploded view of another embodiment of an active infusion transdermal microneedle patch, according to the subject invention. In this embodiment, the actuator compartment and activator compartment are formed as part of an insert that can be operably connected to the body piece.
Figure 12:
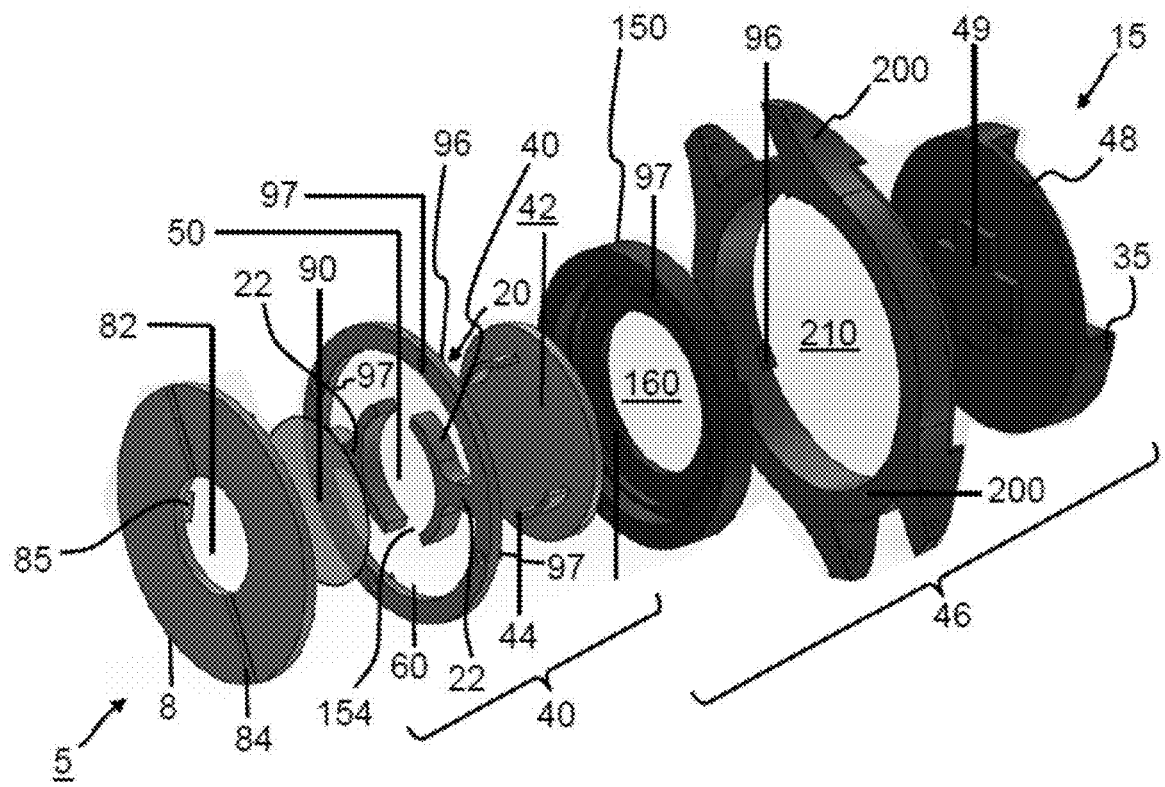
FIG. 12 is an exploded view of yet another embodiment of an active infusion transdermal microneedle patch, according to the subject invention. This embodiment utilizes an insert placed against the body piece to form part of the actuator and activator compartments that are in operable communication.
Figures 13A, 13B, 13C:
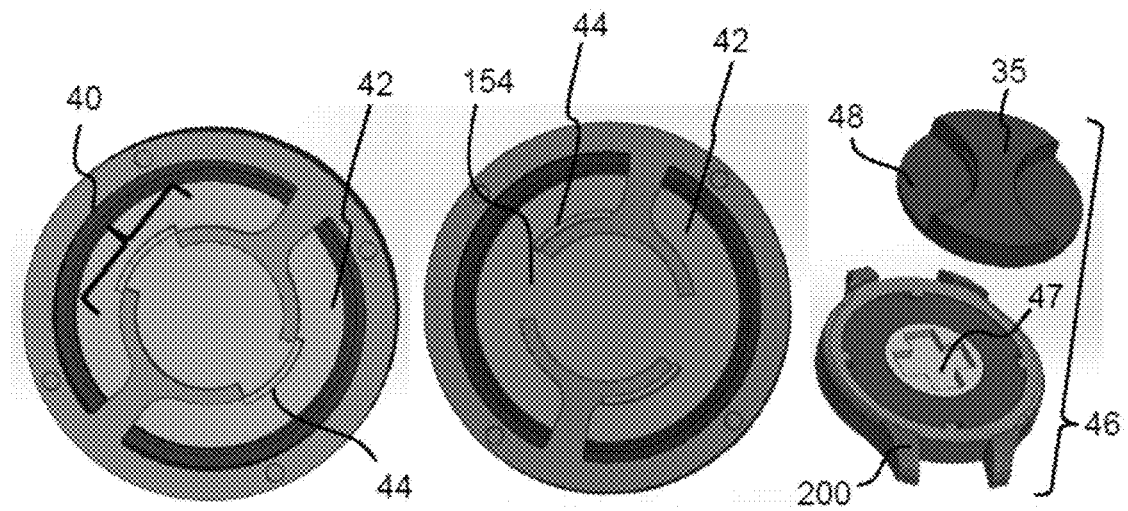
FIGS. 13A, 13B, and 13C illustrate the operation of certain interior components of the embodiment in FIG. 12.

A. General Description of a Transdermal Patch:

In general, a patch design can have one or more reservoirs or compartments for storing therapeutic drug and/or cosmetic formulations. In one embodiment, a body piece overlay 80, an example of which is shown in FIG. 1A, can be configured with at least one drug reservoir 82. In one embodiment, the drug reservoir is open to both the proximal and distal sides of the body piece overlay. The drug reservoir can become sealed during assembly of the patch. In a further embodiment, the body piece overlay 80 can have at least one drug port 84 for injecting one or more drugs into the drug reservoir, usually after the patch is fully or partially assembled. In a further embodiment, the drug port 84 is a channel that extends from the peripheral edge 8 of the body piece overlay to the drug reservoir in the body piece overlay. FIGS. 9, 10, and 12 illustrate examples of body piece overlays 80 with a drug port 84 therein.

Figure 1B:
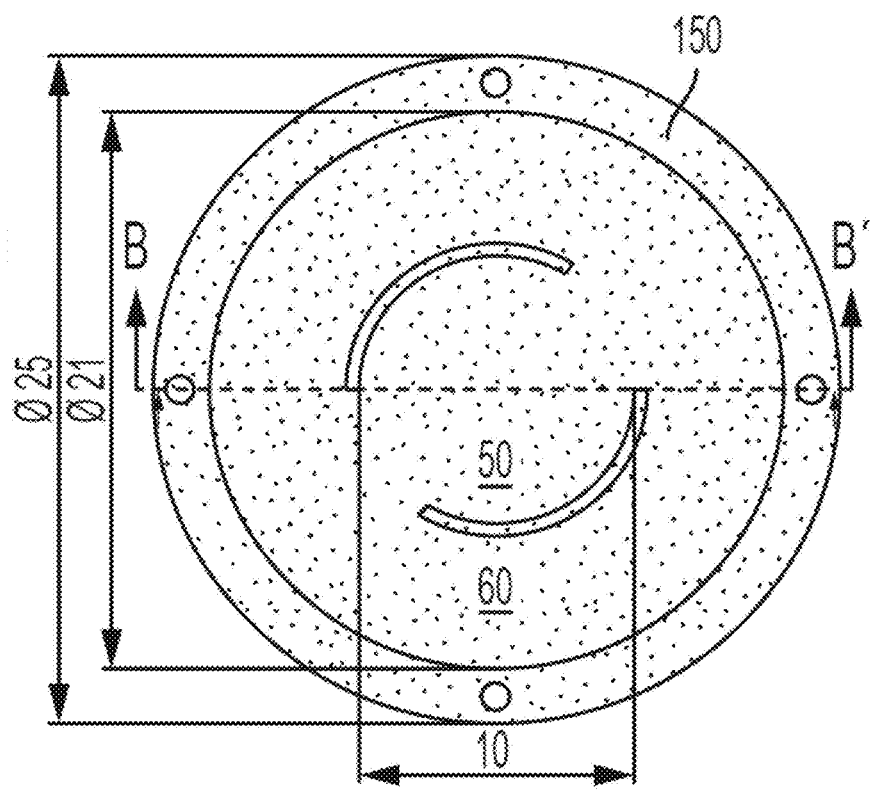
Figure 1C:
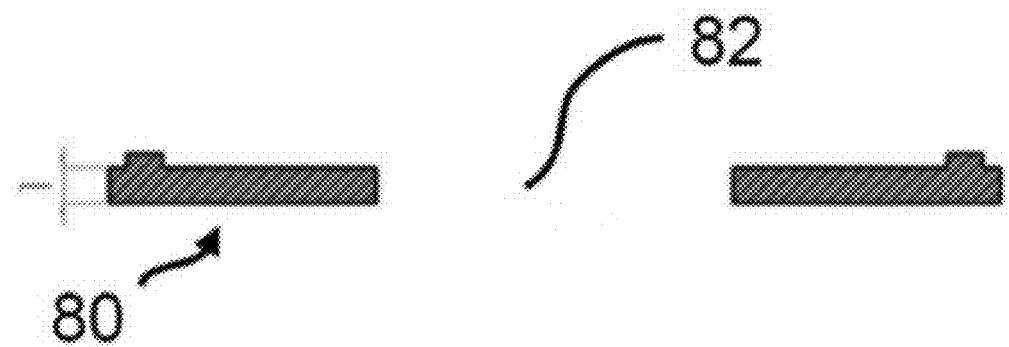
Figure 1D:
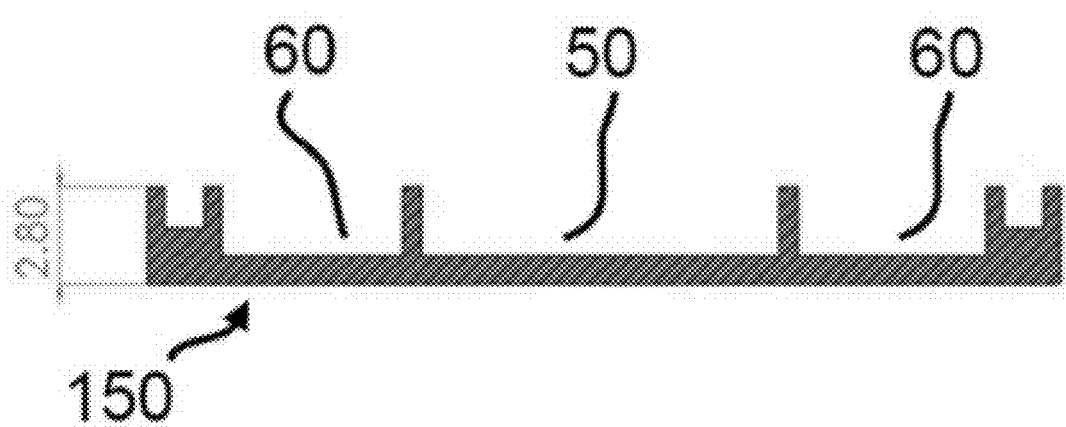
Figure 2A:
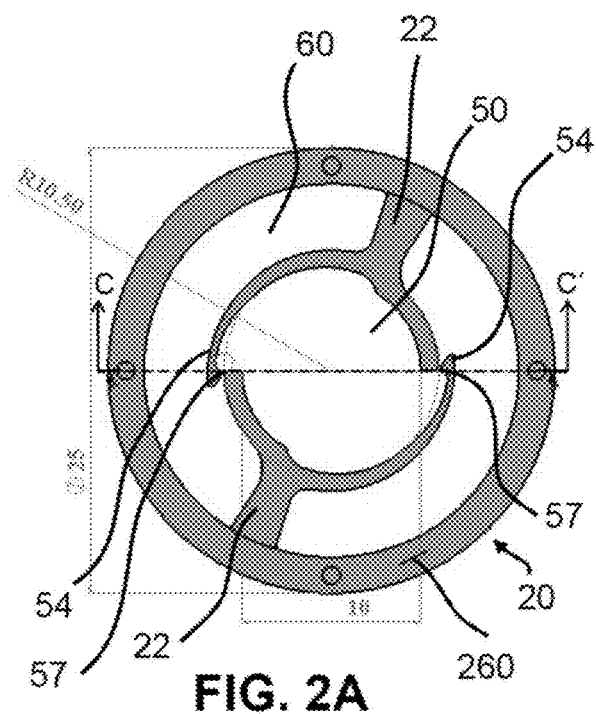
Figure 2B:
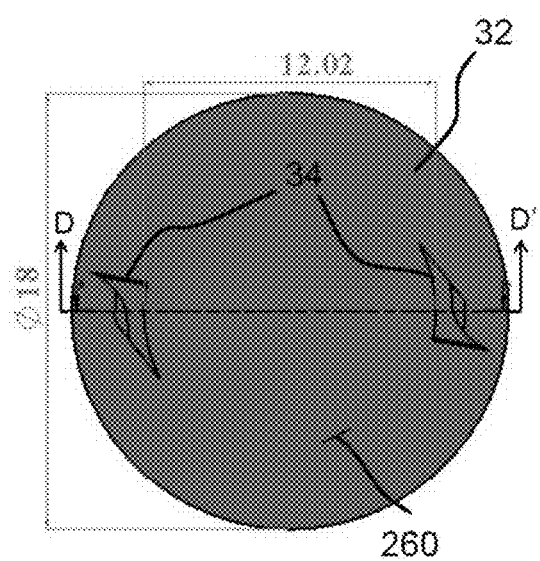
Figure 2C:
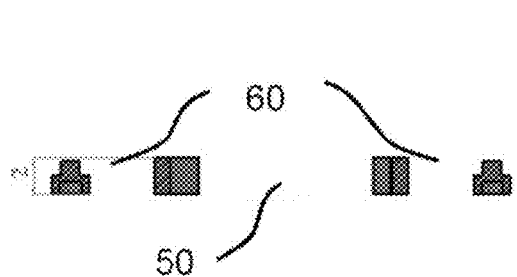
Figure 2D:
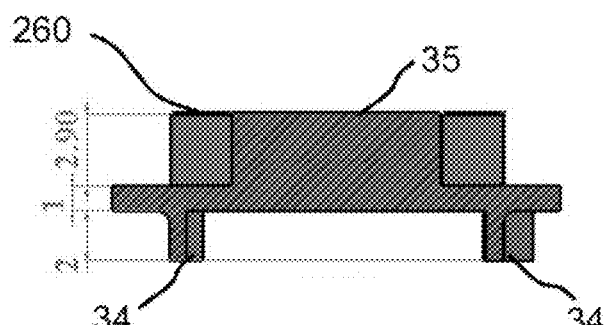
Figure 3A:
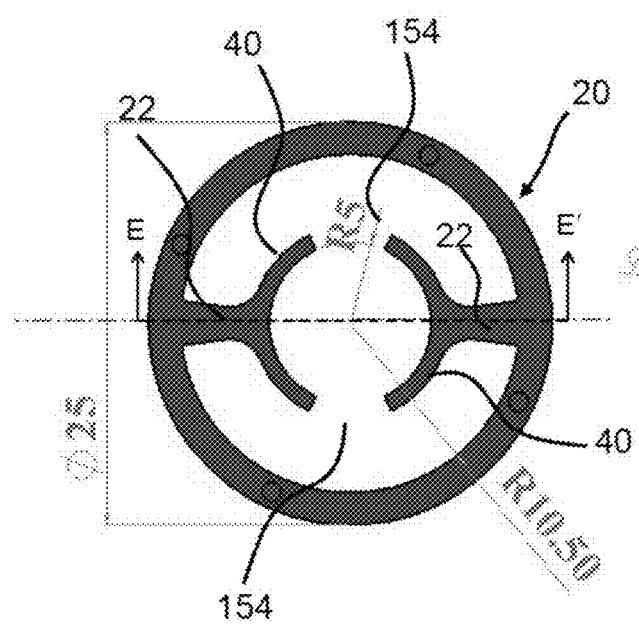
Figure 3B:
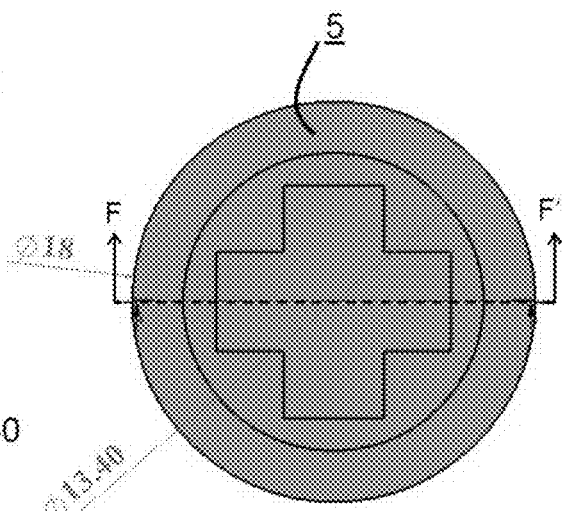
Figure 3C:
Figure 3D:
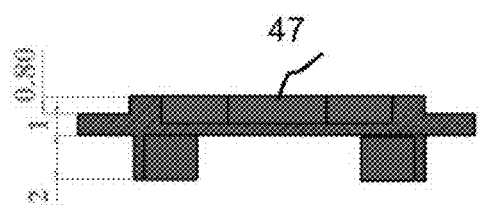

A patch can further have one or more actuator compartments 50 for containing at least one actuator, such as, for example, an expandable hydrogel, and an activator compartment 60, in operable communication with the actuator compartment, which contains an activator, such as, for example water, which is used to trigger hydrogel swelling. FIGS. 1B and 1D illustrate an example of a patch body piece 150 configured with an actuator compartment 50 and an activator compartment 60. In one embodiment, shown in FIGS. 1A and 1B, the storage compartment is approximately 25 mm in diameter and approximately 1 mm thick. In a further embodiment, the actuator compartment, which can contain hydrogel, and the activator compartment, which can contain water, are each approximately 25 mm in diameter and approximately 2.8 mm thick.

Figure 4A:
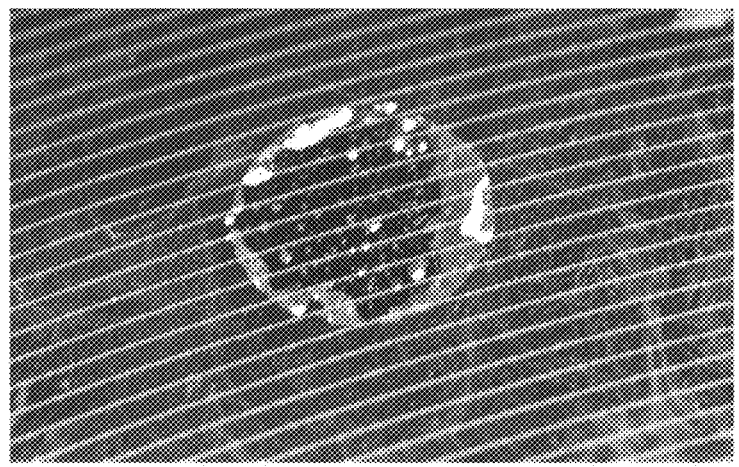
FIGS. 4A and 4B are photographs of a polydimethyl siloxane elastic membrane, according to embodiments of the subject invention.
Figure 4B:
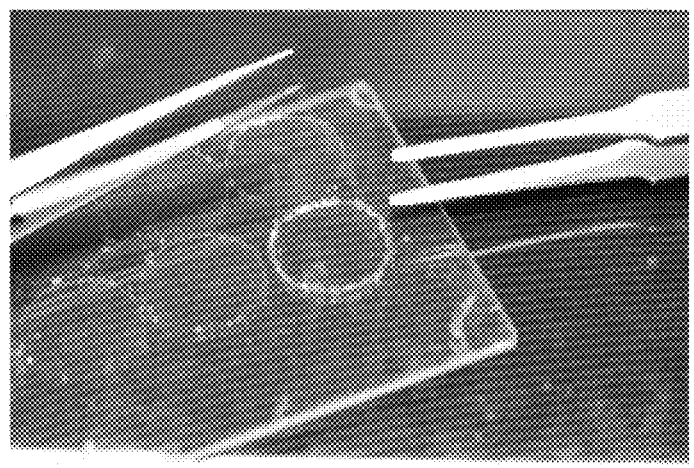

In a further embodiment, the compartments for activator and actuator materials, e.g., hydrogel/water compartments, are separated from the drug reservoir 82 by a membrane 90. The membrane can comprise any of a variety of materials, such as those having an elastic and inert nature. Some non-limiting examples of such material are the Dow membrane (Corning SYLGARD 184), 3M polymer film (COTRAN™ 9722 Polyolefin film or COTRAN™ 9716 EVA film), TEFLON film, polydimethyl siloxane, polyvinyl alcohol or similar materials, or combinations thereof. FIGS. 4A and 4B show an example of a polydimethyl siloxane membrane that has the required thermal and chemical stability and low elastic modulus.

In one embodiment, a polydimethyl siloxane pre-cured mixture was outgassed under vacuum for 30 min. The mixture was spin-coated on a flat glass at ca. 660 rpm for 1 min, and cured at 80° C. for 30 min. Round polydimethyl siloxane membranes of 16 mm diameter were cut from the spin-coated film, as shown in FIGS. 4A and 4B.

Attachment of the membrane to the patch can be achieved by various methods. In one embodiment, an adhesive substance or material was utilized to affix the membrane. For example, a double-sided adhesive tape can be used to affix the membrane to the drug overlay or other patch component. This attachment can also be achieved by using cyanoacrylate with polyolefin primer or by heat sealing. Variations in the materials or methods utilized for attachment of a membrane, such that they do not interfere with or inhibit operation of the patch as described, are within the scope of this invention.

(B) Mechanical Mechanisms for Activating an Actuator:

Typically, the actuator, such as a hydrogel, can be stored within the actuator compartment and can be activated when contacted by or otherwise interacted with the activator, such as water. FIGS. 1A-1D and 9 show an embodiment in which the compartments are formed as part of the body piece 150. In this embodiment, an actuator is stored within an actuator compartment in the body piece. In a further embodiment, the activator can be injected through injector ports 152 within the body piece 150, as shown, for example, in FIG. 9. In one embodiment, the ports are self-sealing, wherein a flexible or elastic material is deposited into the ports. A syringe or needle can be injected through the flexible material to deposit the activator within the activator compartment. When the needle or syringe is removed, the elastic or flexible material of the injector port automatically closes around the opening made by the needle or syringe, to inhibit or prevent the activator from leaking out. Other sealing methods are known in the art and could also be utilized with embodiments of the subject invention, including but not limited to the insertion of a plug or sealant into the port. Agitation of the patch 10 will ensure that the injected activator migrates into the actuator compartment and contacts the actuator to initiate expansion. In a still further embodiment, the actuator compartment has at least one slot 154, which can be referred to as the activator access, therein that allows the activator to migrate, usually uninhibitedly into the actuator compartment.

In an alternative embodiment, the activator compartment 60 and actuator compartment 50 are partially formed as an insert 20 that is disposed within the patch 10 and is operably connecting or abutting the body piece 150. In one embodiment, the actuator compartment is connected to the insert by one or more connector arms 22. When assembled within the patch 10, the actuator compartment formed by the insert can be sealed, so any activator within the operably connected activator compartment is inhibited from contacting the actuator. In a further embodiment, a trigger mechanism is utilized to open the actuator compartment so as to allow contact between the activator and the actuator.

Two exemplary trigger mechanisms, that can be used in various embodiments are shown, for example, in FIGS. 10-14. The trigger mechanisms can be attached to a turnable cover that can be rotated or turned. The trigger mechanisms can disrupt the sealed actuator compartment, so that the activator, such as, for example, water, is released from its compartment to contact the actuator, such as, for example, the hydrogel, which can initiate hydrogel swelling.

One embodiment, an example of which is shown in FIGS. 2A-2D and FIG. 10, utilizes a break gate mechanism 30, having a turnable break gate cover 32 with one or more breaktriggers 34 thereon, and at least one breakable gate 54 as part of the actuator compartment, where the breakable gate can have an arm 57 that forms a seal on the actuator compartment. The break gate cover can be moveably or rotatably adjacent to the body piece, such that it can be turned or rotated relative to the body piece. In a further embodiment, the body piece has an opening 160 that provides access to the break gate cover, so that it can be turned. In operation, when the break gate cover is turned, the break trigger is forced against the arm, it causes the arm to move away from the actuator compartment, opening the actuator compartment to inflow of activator from within the activator compartment.

Figures 11A, 11B:
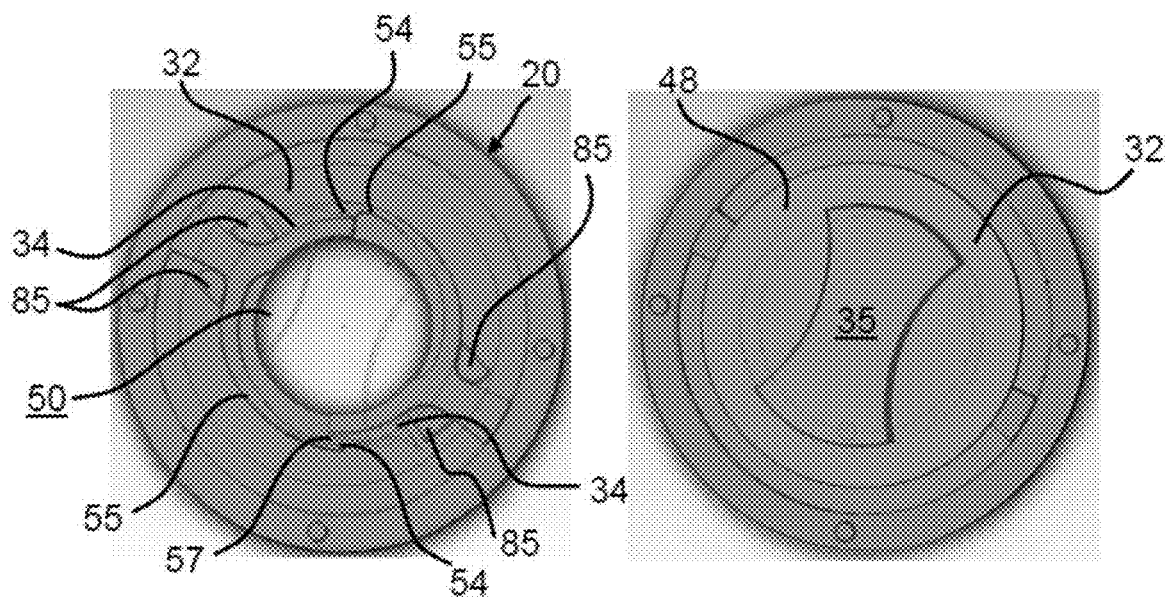
FIGS. 11A and 11B are front and rear plan views, respectively, of certain components used in an embodiment of the active infusion transdermal microneedle patch, shown in FIG. 10.

In one embodiment, the arm applies sufficient force against the actuator compartment to form a sufficient seal. In a further embodiment, the arm and the actuator compartment can have some part thereof formed as an interdigitated profile, which forms a sufficient seal. In an alternative embodiment, the arm and actuator compartment have a frangible attachment 57, which can be referred to as the activator access, therebetween that forms the seal, such that the seal can be broken, cracked, or otherwise disrupted by the break trigger. The break gate cover 32 can also have one or more knobs 35 on the distal side 200 that can be accessed through the opening 210 and used to turn or rotate the break gate cover relative to the body piece 150, forcing the break triggers against the break gates, so as to break, crack, or otherwise separate the breakable gate 54. FIG. 11A shows a non-limiting example of an insert 20 with two breakable gates 54 forming part of the actuator compartment 50, the dashed lines represent the break triggers 34 positioned next to the breakable gates, such that when turned, the break triggers will exert force against the arms, forcing them away from the actuator compartment and permitting activator to flow into the actuator compartment.

An alternative trigger mechanism, shown, for example, in FIGS. 3A-D and 12, utilizes an insert 20, where the actuator compartment has one or more slots 154, similar to those mentioned above. A blocking gate mechanism 40 having a switch cover 42 with at least one switchable gate 44 extending proximally 5 blocks, covers, or otherwise closes the slot, inhibiting activator in the adjacent activator compartment from contacting the actuator. In a particular embodiment, shown in FIGS. 12 and 13, a switchable gate and the actuator compartment are substantially circular, where the switchable gate has a diameter that is slightly larger than the diameter of the actuator compartment, such that a friction fit sufficient to inhibit migration of the activator into the actuator compartment is formed between the switchable gate and the actuator compartment. In an alternative embodiment, the switchable gate can be positioned within the actuator compartment. Activation of the actuator occurs when the switchable gate is rotated, away from the slot 154 in the actuator compartment, as shown, for example in FIG. 13B. To further ensure that the contents of the two compartments remain separated until such time that the switchable gate is moved, a sealant can be used where the switchable gate meets the actuator compartment. In one embodiment, the sealant is a glue that prevents ingress of the activator into the actuator compartment, but which is frangible enough to be broken when the switchable gate is turned or otherwise moved.

It is possible for the switchable gate and actuator compartment to have different shapes, thus, embodiments are not limited to circular or semi-circular configurations. It would be within the skill of a person trained the art to devise alternative shapes and methods by which a switchable gate can be moved away from a slot or some other opening with an actuator compartment. Such variations which provide the same function, in substantially the same way, with substantially the same result are within the scope of this invention.

Figure 14:
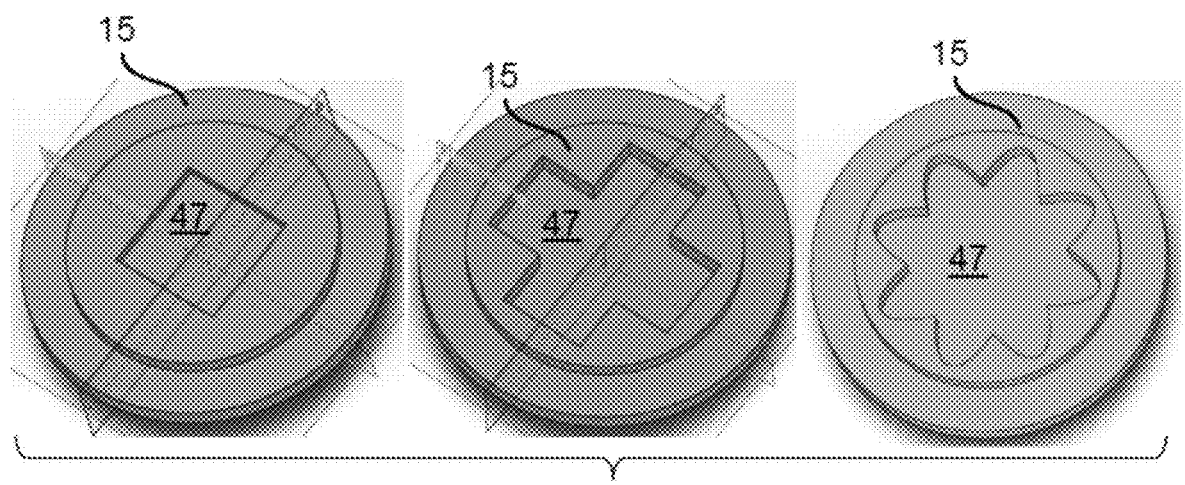
FIG. 14 illustrates alternative boss shape embodiments that can be used for the lock and key components of an embodiment of an active infusion transdermal microneedle patch, according to the subject invention.

In a further embodiment, lock and key mechanism 46 can be used with the switch cover to move the switchable gate 44. In one embodiment, shown, for example, in FIGS. 12 and 13C, the distal side 15 of the switch cover has a lock 47 in the form of a depression having a defined shape. In a further embodiment, a key 48 having a complementary shaped boss 49 that operably connects to the lock. The boss on the key can be fitted into the lock and used to turn the lock 47 in a direction that causes the switch cover to rotate, further causing a switchable gate on the proximal side 5 to rotate as well, opening the actuator compartment within the patch. The key and boss configuration can comprise any of a variety of shapes and sizes. FIG. 14 illustrates some non-limiting examples of alternative shapes that can be used for a lock, in which a complementary boss can be fitted. In another embodiment, there can be multiple locks on the switch cover and a key can be required to the aligned in a specific orientation in order to operably connect with one or more of the multiple locks. In a further embodiment, the key can have one or more knobs 35, mentioned above, to assist in turning the key and boss against the lock. In a further embodiment, the key is removable from the lock, which can reduce the thickness of the patch. This embodiment is advantageous because it allows the key to be removable, reducing the height of the patch, making it more comfortable and less conspicuous to wear. In certain embodiments it also allows more control over the amount of activator that can be released into the actuator compartment. For example, the key can be turned slightly or temporarily to allow some activator to reach the actuator, causing a regulated amount of swelling. If additional swelling is desired, the key can be turned again or for a longer period to allow more, or a greater amount, of the activator to reach the actuator. One or more regulator mechanisms, known to those with skill in the art, can be incorporated into the lock and key mechanism to help control the swelling process. Thus, the rate of swelling can be controlled in certain embodiments.

To ensure that the trigger mechanisms can apply sufficient force against the insert to operably engage with the actuator compartment, it can be beneficial if the actuator compartment is secured in place. This can ensure that the actuator compartment does not rotate and that all of the torque generated by turning of the break gate cover 32 or the switch cover 42 is directed to opening the actuator compartment. To facilitate this, the connector arms 22 can be operably engaged with one or more blocks 85 on the body piece overlay 80. The one or more blocks can abut at least one connector arm 22 preventing the entire insert from being turned. FIGS. 10, 11A, and 12 illustrate embodiments where the body piece overlay 80 has at least one block 85 on the distal side 15 that can be engaged with at least one connecting arm on an insert.

(C) Non-Electric Actuator:

In one embodiment, the non-electronic actuation employed for delivery of stored drug in the patch 10 relies on pH- or solvent-sensitive hydrogels. The hydrogels are usually a network of a hydrophilic polymer that has a large capacity for expansion by absorbing a large amount of liquid, such as water (up to 99.9% of dry weight). The swelling performance and characteristics of a hydrogel are controlled by various parameters, which include, but are not limited to, monomer type, initialization system of polymerization, crosslinker, conjugate, and polymerization method (Deligkais et al., 2010). Zhang et al. modified the microstructure of hydrogel to improve drug release performance by the formation of microgels as primary structure and cross-linking of the microgels into bulk network as secondary structure (Zhang et al., 2010). The release yield of drugs from the modified hydrogel was 4 times higher than that of the conventional one. Due to the high biocompatibility and diverse characteristics of hydrogel, it has been extensively studied for various uses. Kumar et al. reported the use of a pH-responsive hydrogel for oral insulin administration (Kumar et al., 2006).

Hydrogels are well-known in the art for a multitude of uses. Embodiments of the subject invention can employ any of a variety of known hydrogels. Some non-limited examples of solvent-sensitive hydrogels that can be used with embodiments of the subject invention, include poly acrylamide-polyethylene glycol-maleic acid, poly(acrylamide-co-butyl methacrylate), poly acrylamide-polyethylene glycol-maleic acid, poly acrylamide-polyethylene glycol-bovine serum albumin, and others. Other non-limiting examples of pH-sensitive hydrogels that could be employed with embodiments of the subject invention are polyvinyl alcohol-polyacrylic acid, poly(n-isopropylacrylamide-co-acrylamide), poly(methacrylic acid-co-ethylene glycol), and others. Gu et al. (Gu et al., 2007) demonstrated that the incorporation of carboxyl groups into poly(N-isopropylacrylamide) matrix led to response to pH. A person with skill in the art will be able to determine an appropriate hydrogel, or similarly characteristic substance, from those known in the art. Such variations which perform substantially the same function, in substantially the same way, with substantially the same result are within the scope of this invention.

(D) Microneedles:

Microneedles have been developed for drug delivery application (see, for example, U.S. Pat. Nos. 8,162,901; 8,197,435; 8,062,835; 8,043,250; 8,150,505; and 7,798, 987). Any of the materials known for microneedle fabrication, such as, but not limited to, silicon (see, for example, U.S. Pat. Nos. 3,964,482; 7,332,339; 6,844,213; 5,312,456; and 7,588,552), metals (see, for example, U.S. Pat. Nos. 8,137,736; 7,097,776; and 7,497,980, as well as U.S. Published application no. 2011/0237925), polymers (see, for example, U.S. Pat. Nos. 6,334,856; 6,924,087; and 6,451, 240; and U.S. Published Application no. 2006/0055090, as well as Yung et al., 2012) and ceramics (see, for example, U.S. Pat. No. 7,699,819), and other materials or combinations thereof, are compatible for use in the present invention.

Figure 8A:
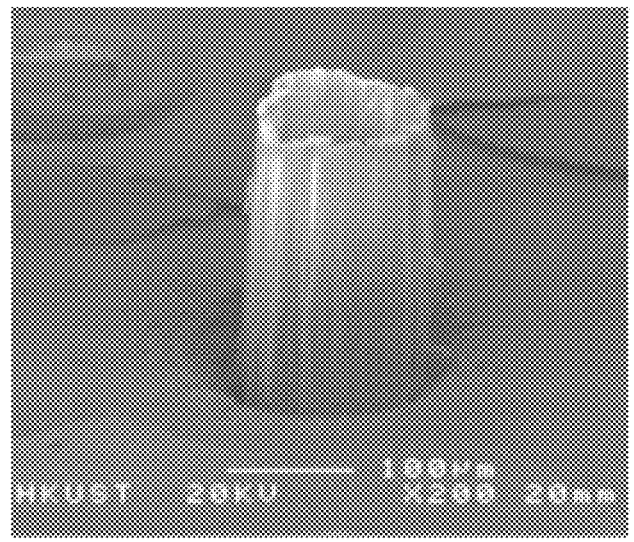
FIGS. 8A, 8B, and 8C are photographs showing a zeolite, plastic, and commercial microneedle plates, respectively.
Figure 8B:
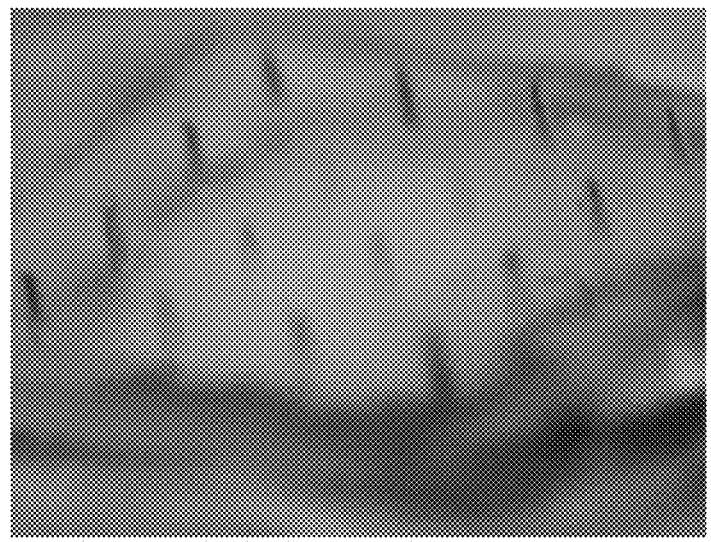
Figure 8C:
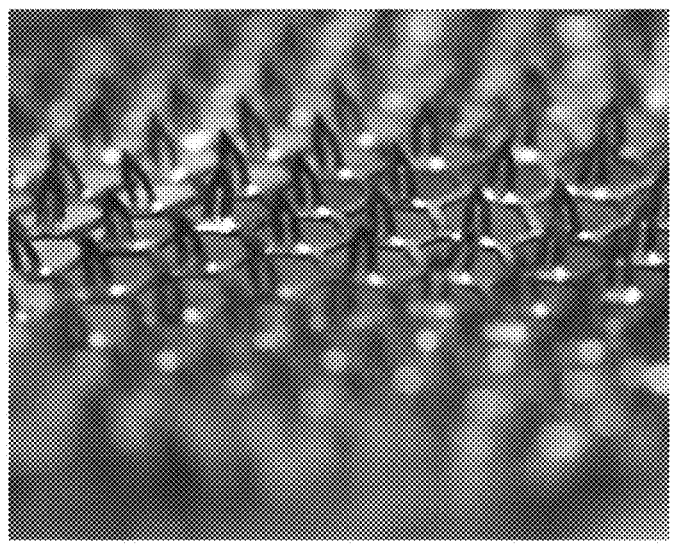

The manufacture of microneedles is well-known in the art, with several techniques being documented. Silicon is widely used as a material in the microelectronics industry, where the processes for using silicon, particularly for microneedle production, are well-known and quite mature. Metal is another common material used for microneedle production, that advantageously provides good mechanical strength. Polymers are also employed as a material for microneedles, usually because of good biocompatibility characteristics. FIGS. 8A, 8B, and 8C are photographs of examples of zeolite, plastic, and commercial microneedles that can be used with embodiments of the subject invention. The heights of zeolite, plastic, and commercial microneedles are about 150 μm, 500 μm and 600 μm, respectively. A zeolite microneedle plate can be fabricated from a backside UV exposure with a non-transparent pre-coated substrate, while a plastic microneedle plate can be fabricated by micro-injection moulding, such as taught by Yung et al. (Yung et al, 2012). Thus, various methods of manufacturing microneedles having various characteristics are well-known in the art.

Typically, in use, microneedles are utilized to puncture or penetrate the skin, so as to reach at least the dermis layer of the skin. A single microneedle can be utilized or a plurality of microneedles can be utilized. The embodiments of the subject invention can also utilize either a single microneedle or a plurality of microneedles. The material used, the size, and the numbers of microneedles utilized with the different embodiments of a patch of the subject invention are factors that can be determined by a person with skill in the art. Such variations which provide the same function, in substantially the same way, with substantially the same result are within the scope of this invention.

The attachment of a microneedle or microneedle plate to a patch can be accomplished by a variety of devices and techniques. Usually, the microneedle support or microneedle plate is affixed to the proximal side of the body piece overlay and over the drug reservoir therein. In one embodiment, a microneedle plate is attached using silicone adhesive or cyanoacrylate bonding. Variations in the method or devices utilized for attachment of a microneedle to a patch 10 are within the scope of this invention.

(E) Wearable Patch Housing:

A transdermal patch of the subject invention can transmit one or more drugs through the skin. Typically, transdermal delivery results in a drug ultimately being delivered into the bloodstream, though this is not always necessary, or it may not be a direct transmission. To effect transdermal delivery of a drug, the embodiments of the patch of the subject invention are usually placed into contact with the skin. One method is to use techniques or devices that attach a patch directly to the skin, such as, by way of non-limiting examples, adhesives or sutures. Alternative embodiments employ devices that hold or press a patch into close proximity to the skin.

Figure 21A:
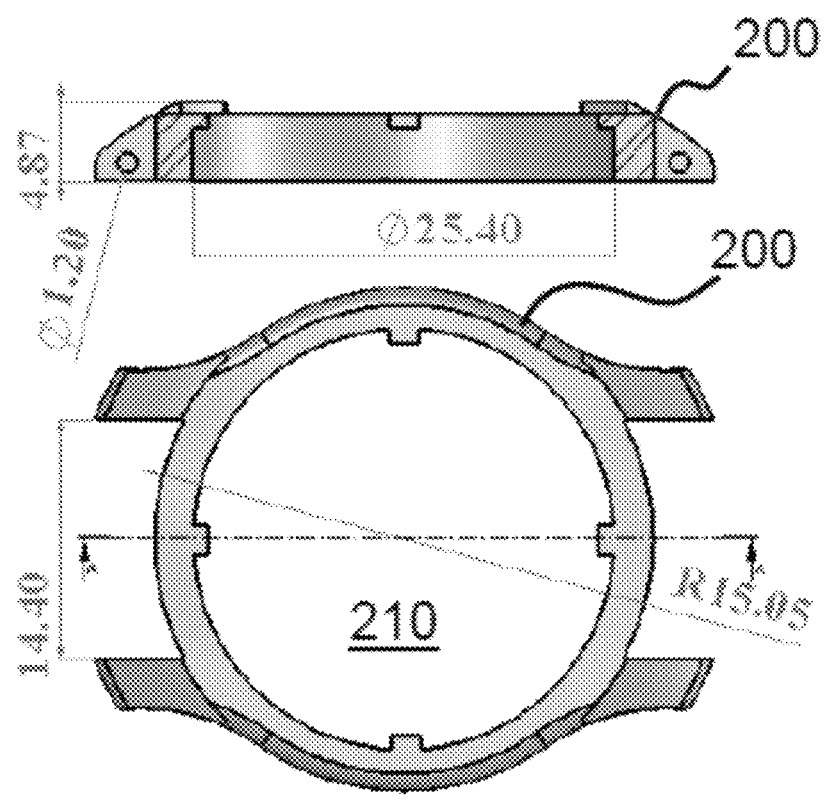
FIGS. 21A and 21B illustrate an embodiment of a wearable patch, according to embodiments of the subject invention.
Figure 21B:
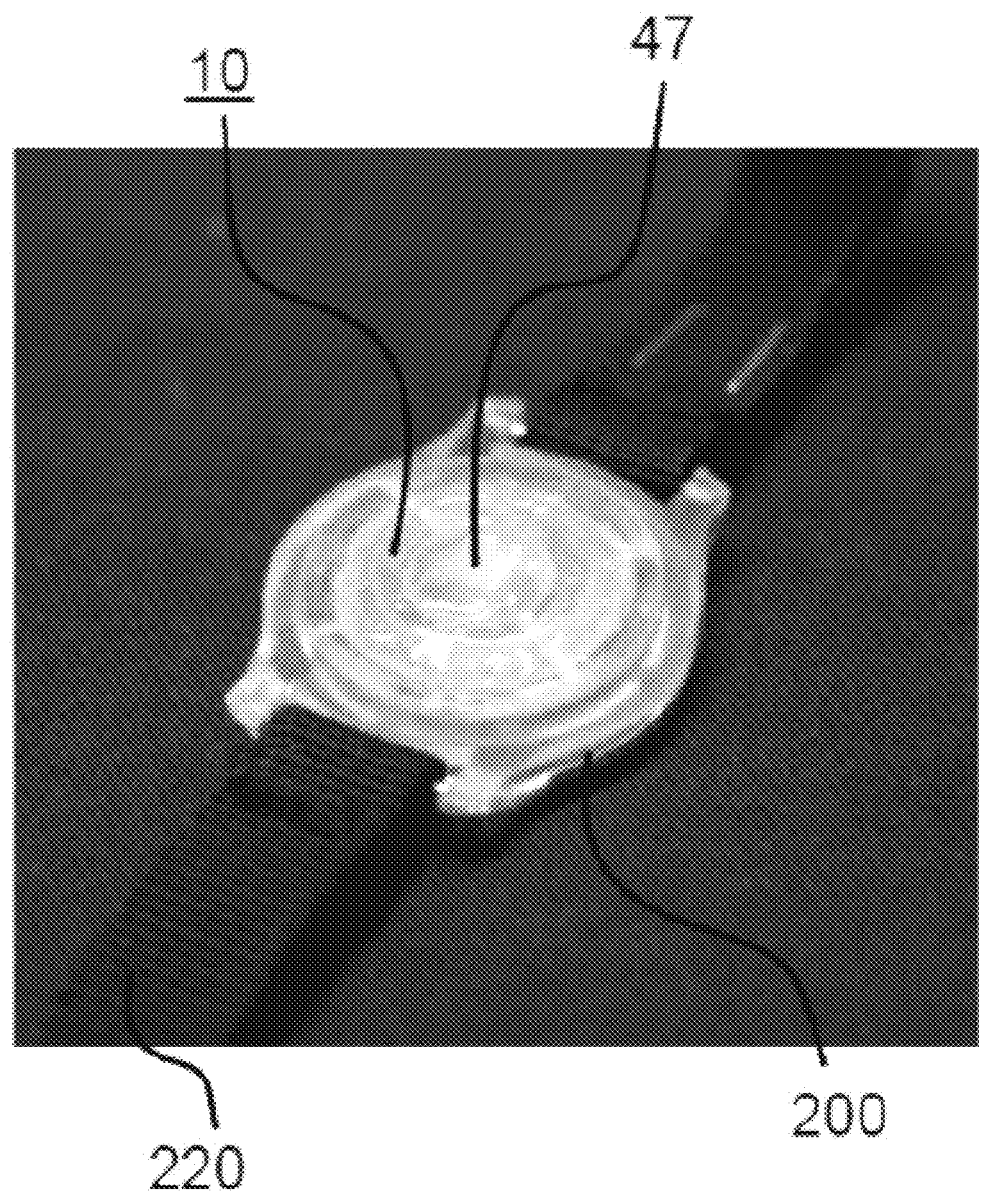

In one embodiment, a patch is incorporated into a wearable housing 200 that could be worn on the body and/or limbs. A housing can comprise a manufactured cavity for containing the patch and one or more attachment devices for securing it in close contact with the skin. FIGS. 21A and 21B illustrate one embodiment of a housing in which a patch embodiment can be secured and placed against the skin. In one embodiment, the wearable housing is made of any suitably rigid or semi-rigid material, including, but not limited to, metals, plastics, or ceramics, glass, rubber, wood products, and combinations thereof, etc. In a further embodiment, the housing has an opening 210 in the distal side that operably communicates the proximal side 5 with the distal side 15, so that a lock 47 is accessible through the body piece 150 with a key 48.

In a further embodiment, one or more attachment devices 220 can be utilized to secure the housing next to the skin. Such attachments devices can be removable and, in a further embodiment, are adjustable.

(F) Alignment Features:

The trigger mechanisms employed with certain embodiments of the subject invention can require that certain components of the patch be properly aligned to function within the device. Depending upon the method of manufacture and/or assembly of the patch components, alignment may be automatic or may require visual or tactile cues on the various components indicating their proper alignment in the overall assembly.

Embodiments of the subject invention use alignment structures to ensure that the components of the patch are properly aligned. In one embodiment, components are aligned by means of a fixed fastener mounting method. With this embodiment, one component is configured with a groove or bore 96 and another component is configured with a compatible tab 97. To assemble the components the tab and bore can simply be aligned and the two components pushed together, so that the tab inserts into the bore. In a specific example, shown in FIGS. 10 and 12, the insert 20 is configured on one side, nearest the body piece 150 with tabs 97 and with bores 96 on the opposite side, nearest the body piece overlay 80. When the tabs and bores on the insert are aligned with their respective components on the patch, so that the tabs can be inserted into the bores, the internal components will also be aligned so they can operate as described above.

It is within the skill of a person trained in the art to devise numerous methods by which the components of a patch embodiment can be properly configured and aligned. Any such variations are within the scope of this invention.

(G) Leak-Prevention Coatings:

The embodiments of the subject invention require that the activator and actuator devices and/or substances remain separated until such time that the patch device is ready to be utilized for drug delivery. While the components of the embodiments are designed to operably connect to achieve this function, it can be helpful if the points of juxtaposition of certain components include additional materials to prevent leakage.

In one embodiment, components of the patch embodiments are at least partially covered with a coating 260 of one or more materials that can form a seal or barrier between the components when a patch is assembled. In one embodiment, the components, i.e., the insert and the body piece are coated with a silicon-based substance that can be compressed between the two components during assembly to form an impervious seal. Other substances that can be utilized include, but are not limited to, rubber, soft metals, plastics, ceramics, wood products, nylon, and other partially deformable materials, or combinations thereof. Alternatively, certain components can be secured with adhesives, heat sealing, cold sealing, friction fit, or other sealing methods. It is within the skill of person trained in the art to determine any of a multitude of materials and methods that can be utilized to form a sufficient seal between components of the embodiments of the subject invention. It will be understood that such variations are within the scope of this invention.

Following are examples that illustrate procedures for practicing the subject invention. These examples are provided for the purpose of illustration only and should not be construed as limiting. Thus, any and all variations that become evident as a result of the teachings herein or from the following examples are contemplated to be within the scope of the present invention.

EXAMPLES

Example 1: Manually Activated Nonelectronic Active-Infusion Transdermal Patch An active-infusion transdermal patch for drug delivery was tested, where the patch included a hydrogel compartment, water compartment, plastic membrane, drug reservoir and microneedle plate. FIGS. 1A-1D and 9 illustrate components utilized with the patch for this test. The hydrogel compartment and activator compartment were formed as part of a backing component. In this test, a dried hydrogel was placed into the hydrogel compartment, with slots that open into the activator compartment. A chemically-inert plastic membrane was adhered between the hydrogel compartment and a body piece overlay with a drug reservoir therein. The membrane separated the compartment and reservoir to prevent contact of the drug with the hydrogel. The activator compartment surrounded the actuator compartment with the hydrogel to contain sufficient activating agent (i.e., water) to swell the hydrogel. The activating agent was injected into the activator compartment through two resealable injector ports within the body piece. The body piece, which caps the distal end 15 of the compartments containing hydrogel and water, acts to withstand the swelling force of the hydrogel, causing the hydrogel to swell in a proximal direction towards the drug reservoir. A plate grown with microneedles was sealed over the drug reservoir, on the opposite, proximal, side 5 from the membrane, in order to facilitate transdermal delivery.

A pre-determined amount of a drug solution was loaded into the drug reservoir by syringe needle through the drug ports in the body piece overlay. To initiate drug delivery, activator, (in this case, water) was injected into the activator reservoir through the injector ports. The device was then shaken gently to allow proper contact between the swelling agent and dried hydrogel actuator. The dried hydrogel then swelled in a time-controlled manner. Volume expansion of the hydrogel caused the elastic membrane to be pushed towards the drug reservoir and forced the drug out of the reservoir through the hollow microneedles. It is expected that installation of the patch onto a patient would cause the expelled drug to be deposited to deep skin layers. The overall dimensions of the patch were 25 mm in diameter and 4 mm in height.

Example 2: Nonelectronic Active-Infusion Transdermal Patch Utilizing Breakable Gate Compartment An active-infusion transdermal patch for drug delivery was tested, where the patch included a design that was similar to that utilized in Example 1, but which allows for storage of all necessary activators, actuators, and drugs within the patch device. FIGS. 2A-2D and 10 illustrate patch components utilized with this test, wherein FIG. 10 is an expanded view of a modified active infusion transdermal microneedle patch. Note that the microneedle plate is not shown in these figures, but was attached to the body piece overlay as shown in FIG. 9.

With this patch design the actuator and activator compartments are formed by a divided insert that is positioned between the body piece overlay the body piece. The actuator compartment is formed with two moveable arms. The drug delivery mechanism was the same as that utilized with the mechanical patch, described in Example 1, wherein the drug was then loaded into the drug reservoir by syringe needle through the two resealable injector ports. Hydrogel actuator and water swelling agent were loaded into their respective reservoirs, after the plastic membrane and the insert were mounted on the drug reservoir in the body piece overlay, as shown in FIG. 10. A turnable break gate cover having two break triggers was then placed over the insert, and the body piece was placed over that, with the knob on the break gate cover accessible through the body piece. Alignment structures were used to correctly position the body piece with the insert, such that the break triggers were correctly aligned with the arms of the actuator compartment. FIGS. 11A and 11B show plan views of the active infusion transdermal microneedle patch utilized with this test. The water blocking gate in the hydrogel reservoir included two moveable arms. The turnable break gate cover included two break triggers. Blocks on the distal side of the body piece overlay, facing the insert, fit on either side of the connector arms to hold the insert in place, ensuring all torque generated by turning of the break gate was transmitted to the frangible attachment forming the seal. The seal was broken via turning the knob on the break gate cover. By properly shaking the patch, swelling agent in actuator compartment made contact with the dried hydrogel at the center to trigger hydrogel swelling, causing the membrane to push into the drug reservoir, which in turn forced the drug out of the microneedles, and hence drug delivery. The overall dimensions of the patch in this test were 25 mm in diameter and 6.9 mm in height.

Example 3: Nonelectronic Active-Infusion Transdermal Patch Utilizing a Blocking Gate Mechanism An active-infusion transdermal patch for drug delivery was tested, where the patch included a design that was similar to that of Example 2, but which utilized a switch cover with at least one switchable gate that opens the actuating compartment. FIGS. 3A-3D and 12 illustrate patch components utilized with this test, wherein FIG. 12 is an expanded view. Note that the microneedle plate is not shown in FIG. 12, but was positioned in the same location as shown in FIG. 9, i.e., proximal to the body piece overlay, over the drug reservoir.

For this test, the insert was configured with a blocking gate mechanism that included a switch cover with switchable gates extending from the proximal side, as shown, for example, in FIG. 12. The switchable gates were used to close two slots within the actuator compartment. The actuator compartment was attached to the insert by connector arms.

The switchable gates were positioned over the slots in the actuator compartment, to prevent the contents of the activator compartment from making undesirable contact with the contents of the actuator compartment. To further ensure that the contents of the compartments remained initially separated, the junctions between switchable gates and the actuator compartment were sealed with epoxy resin to ensure complete isolation of swelling agent in the activator compartment, inhibiting it from reaching the hydrogel in the actuator compartment.

The proximal components of the patch were assembled similar to those in Example 1 and Example 2. However, this embodiment was employed with a housing having alignment points complementary to or that correspond to alignment points on the back cover. The housing provided proper positioning and holding of the patch in axial and tangential directions. The alignment points were used to ensure that the switchable gates were positioned and secured over the slots in the actuator compartment during assembly of the patch.

The housing had an opening that allowed the lock of the switch cover to be exposed to the distal side of the housing. The switch cover was configured to operate as part of a lock and key mechanism. The lock, which was a shaped depression in the distal side of the body piece, was compatibly shaped with a boss on the proximal side of a key, shown for example in FIGS. 12, 13C, and 14.

To activate drug delivery, the key was pressed into the lock and turned counter clockwise, which simultaneously rotated the switchable gates away from the slots in the actuator compartment. Note, the key and switchable gates could have been configured to be turned clockwise as well. Activator was then able to flow into the actuator compartment, initiating swelling of the hydrogen therein. The switch cover acted to resist the swelling hydrogel, forcing all of the swelling motion to be directed towards the drug reservoir and the microneedle plate.

The key utilized in this test had a diameter of 25 mm and a height, from the proximal to the distal side of 5 mm. The patch utilized in this test, without the key in place, had a diameter of 25 mm and 4.8 mm in height.

Example 4: Water-Proofing, Leak-Proofing and Assembly

For the purposes of testing, to ensure that the activator did not prematurely contact the actuator, the components of the patch were formed with one or more seals. The patch compartments, trigger mechanisms, and optionally, the microneedle plate were coated with a biocompatible water-proofing layer to provide leak-free seals. For testing the patch, a silicone coating was made from a mixture of silicone and a curing agent (50:1 w/w ratio), cured at 60° C. for 4 h.

Further, a double-coated adhesive tape, that is, one with adhesive on two sides, was cut in a circular shape and attached distal to the drug reservoir, between the body piece overlay and the actuator or hydrogel compartment. The area of the adhesive tape exposed to the drug reservoir was trimmed out and a plastic membrane was then attached to the remaining adhesive tape. Next, a prepared hydrogel was fitted into the hydrogel compartment. The drug reservoir was aligned with the hydrogel compartment by means of alignment structures and bonded in place with an adhesive to ensure a leak-free seal. A microneedle array plate was attached by direct bonding to the proximal side of the body piece overlay to form a drug reservoir between the membrane and the microneedle plate. The microneedle plate can be attached by any of various means, for example, by using silicone adhesive or cyanoacrylate bonding Example 5: Preparation of Hydrogel Solvent-sensitive hydrogel, PAAm-PEG4000, was synthesized by free radical polymerisation and used in the patch embodiments of the current invention. 15 wt % acrylamide (AAm), 2 mL of 0.014 M ammonium persulfate (APS), 2.4 mol % N,N'-methylenebis(acrylamide) (MBAAm), and 9 wt % polyethylene glycol with molecular mass of 4,000 g/mol (PEG4000) was gently mixed in 7 mL deionized water (DI) water (Caykara et al., 2006). The mixture was degassed with nitrogen for 10 min. Then, 1 mL of 0.08 M tetramethylethylenediamine (TEMED) was added to the mixture with stirring. The mixture was quickly poured into a plastic cylinder with inner diameter of 11 mm and was allowed to settle for polymerization. The open end of the cylinder was covered with parafilm 5 min after the start of reaction. The cylinder was allowed to stay overnight for complete reaction. After that, the hydrogel was cut into smaller pieces, with the help of a spacer. The width of the spacer was set to 3.6 mm, for which the accuracy was measured by an electronic calliper. The hydrogel was then washed with DI water for a week to remove unreacted substances. The hydrogel pieces were dried under vacuum for 2 days. The dried hydrogel had dimensions of 6.47±0.03 mm in diameter and 1.7 mm±0.1 mm in height.

Example 6: Hydrogel Surface Coating

Figure 6:
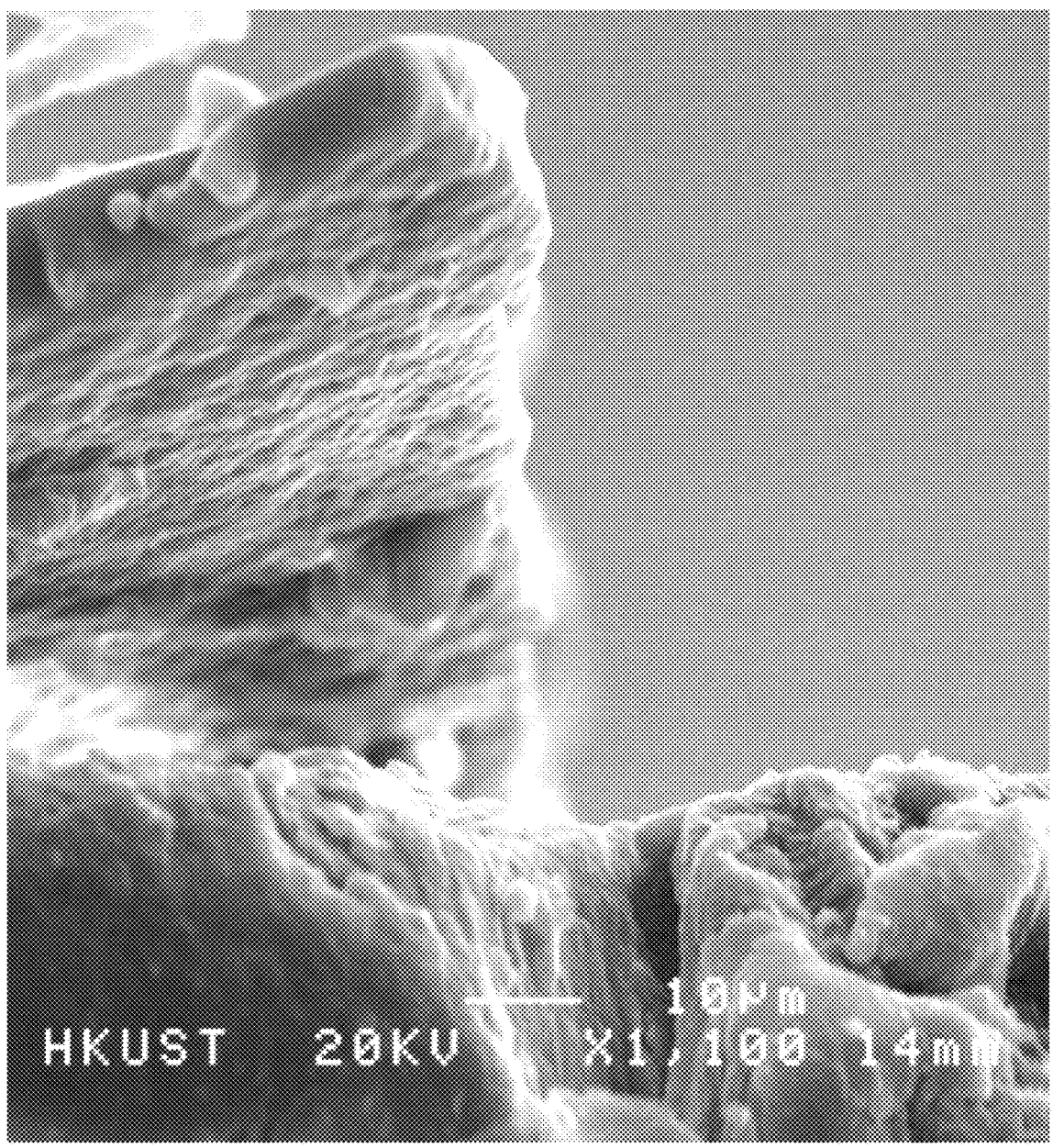
FIG. 6 is an SEM image of a cross-sectional view of a polydimethyl siloxane-coated hydrogel.
Figure 7:
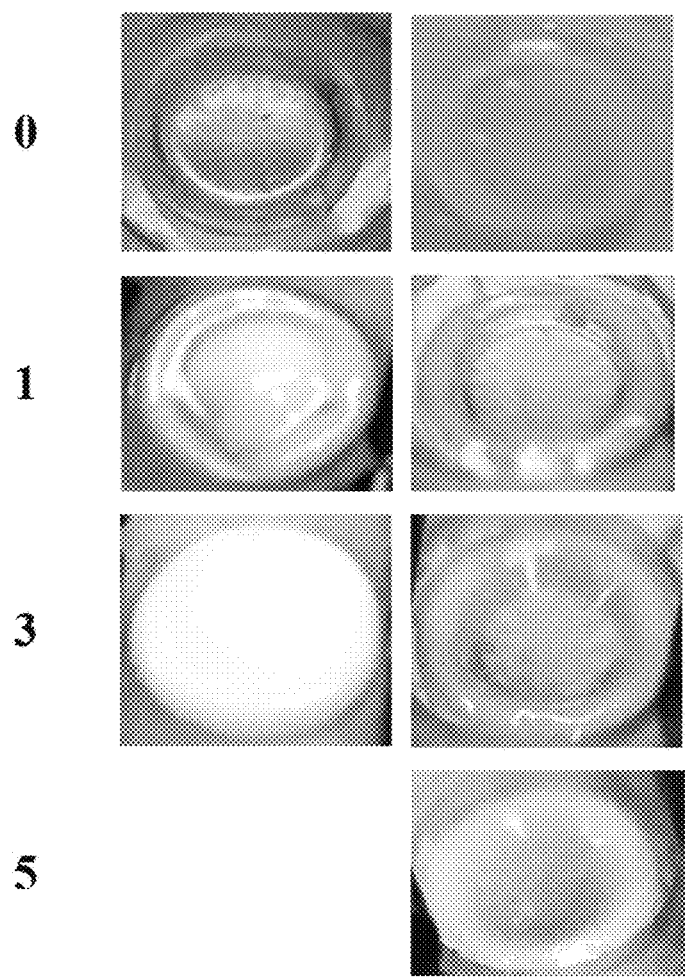
FIG. 7 is a table demonstrating the swelling characteristics of uncoated and spray-coated hydrogels over a time period of 5 hours.

A dried hydrogel from Example 5 was spray coated. Polydimethyl siloxane was weighed and mixed with 10% w/w curing agent to form a pre-cured mixture. Equal weight of hexane was added to the mixture to lower the viscosity. The mixture was then poured into a sprayer with a spraying pressure 0.2 kgf/cm$^2$, placing 0.3 m above the hydrogel. The dried hydrogel was sprayed with the mixture for 10 sec. After 2 min of settling, the hydrogel was heated in an oven at 80° C. for 30 min. The hydrogel was then turned over and the entire process repeated on the uncoated side of the hydrogel. The spray-coated hydrogel was stored in a desiccator. FIG. 6 is a SEM photograph of a cross-section taken from a spray-coated hydrogel.

Example 7: Hydrogel Swelling, Performance, and Behaviour

Figure 5:
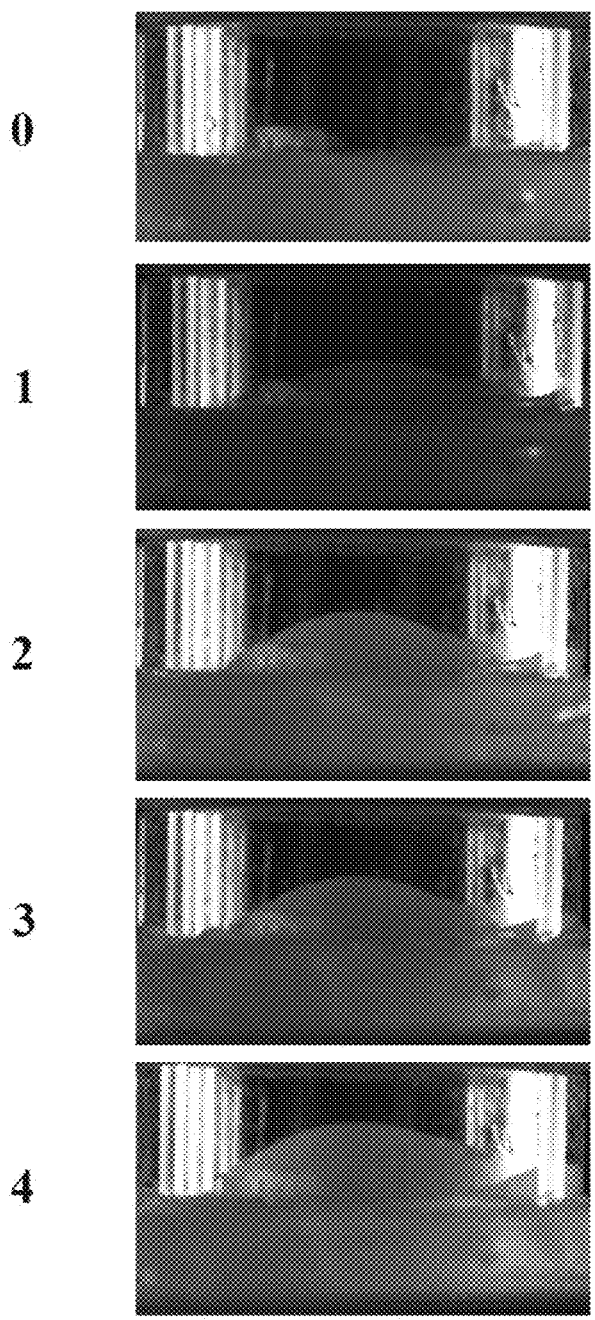
FIG. 5 is a table demonstrating the swelling characteristics for an uncoated hydrogel, according to embodiments of the subject invention, over a time period of 4 hours.

The uncoated hydrogel swelling properties were observed with a mock setup. For the mock set-up, a transparent activator compartment for water and an actuator compartment for hydrogel were created and placed on a hard surface, and a transparent drug reservoir was placed at the top, as illustrated in FIG. 5. A polydimethyl siloxane membrane was placed between the hydrogel and the drug reservoir. A dried hydrogel was put inside the hydrogel compartment. Weight was applied on top of the drug reservoir to hold the assembled substrates in place. DI water was added to the water reservoir to initiate hydrogel swelling. Photos were taken hourly for 8 hr after water addition (Canon 40D with EF-S 60/F2.8 macro lens, Sea & Sea YS-110 strobes*2, TTL controlled). FIG. 5 illustrates a photo-graphic progression of the uncoated hydrogel swelling property over time. Hydrogel started swelling, after the addition of water, reached about half the height of the drug reservoir in 2 hr, and then swelled very slowly afterward. The result clearly indicates that the swelling force from the hydrogel is sufficient to expand and force the polydimethyl siloxane membrane toward the drug reservoir. However, the swelling process of the uncoated hydrogel is considered too fast for long-term drug delivery (e.g. 8 hr). To achieve a slower, more controlled hydrogel swelling, a spray coating step was carried out, as described in Example 6. To verify the coating of polydimethyl siloxane onto the hydrogel, a spray coated sample was examined under scanning electron microscope (SEM). The SEM photograph in FIG. 6 shows that polydimethyl siloxane of a thickness of 51.7 μm was coated onto the hydrogel by the method described above.

FIG. 14 is a series of photographs showing the swelling property of a spray-coated hydrogel compared with an uncoated hydrogel. Despite the difficulty in quantifying the volume expansion of the hydrogel by camera, the prolonged swelling process after coating was clearly observable. It is believed that the polydimethyl siloxane coating constrains water contact of the dried hydrogel, but the water contact triggers the hydrogel to swell eventually. Volume expansion of the hydrogel breaks the coating layer, allowing more water to diffuse and interact with the hydrogel.

Example 8: In-vitro Study

Porcine ear skin was used as the delivery barrier in an in vitro experiment, because of the similar histological and physiological properties to human skin (Ah et al., 2010 and Yan et al., 2010). Porcine ears were freshly obtained from a local slaughter facility, gently washed with running tap water, and chopped into pieces of 50 mm in width. Visual observation was done to check if the skins were free from lesions and infections. Hairs at the back of the ear were carefully removed by clipper. Full thickness skins were obtained using manual-operated dermatome with uniform insertion force and angle. The split skins were cut into discs with 40 mm diameter. The skins were then sprayed and rubbed with 75% ethanol for 1 mm to remove fatty tissues and dirt, followed by DI water washing. Thereafter the skins were blotted with a cellulose-based fiber tissue, such as KIMWIPES™, wrapped with aluminum foil, and stored in a −20° C. refrigerator until further use. All prepared porcine skin was used within 2 weeks.

Vertical diffusion cell was filled with 7 mL phosphate buffered saline (PBS) (137 mM sodium chloride (NaCl), 2.7 mM potassium chloride (KCl), 4.3 mM sodium phosphate dibasic heptahydrate ($NaH_2PO_4.7H_2O$), and 1.6 mM potassium phosphate monobasic ($KH_2PO_4$), pH 7.4) and pre-run at 300 rpm with bath circulator for 1 hr to achieve 37° C. Porcine skin was thawed by soaking in PBS at room temperature for 1 hr. After that, the porcine skin was mounted between the receptor and the donor cell of the diffusion system. The stratum corneum of the skin faced the donor cell while the dermis side faced the receptor cell. The skin was handled with care to avoid bubble accumulation on the receptor side of the skin. Diclofenac sodium (DFS) or insulin (70 μL) and DI water (500 μL) were loaded into the drug and water reservoirs, respectively, through the resealable injector ports. A patch, such as those described in previous examples, was gently shaken to ensure water could make contact with the dried hydrogel inside. The patch was applied on the donor side of the skin by finger force, with the help of adhesive tapes to keep the patch in position. Samples (1 mL) were withdrawn from the receptor cell every hour with immediate replenishment of the same volume of fresh PBS. The tests were done with patches bonded with commercial (ME-C-600), zeolite (SSM-O-150), or plastic (P-O-500) microneedles.

Example 9: In-Vitro Study Using NSAID Drug Diclofenac Sodium (DFS)

Figure 16:
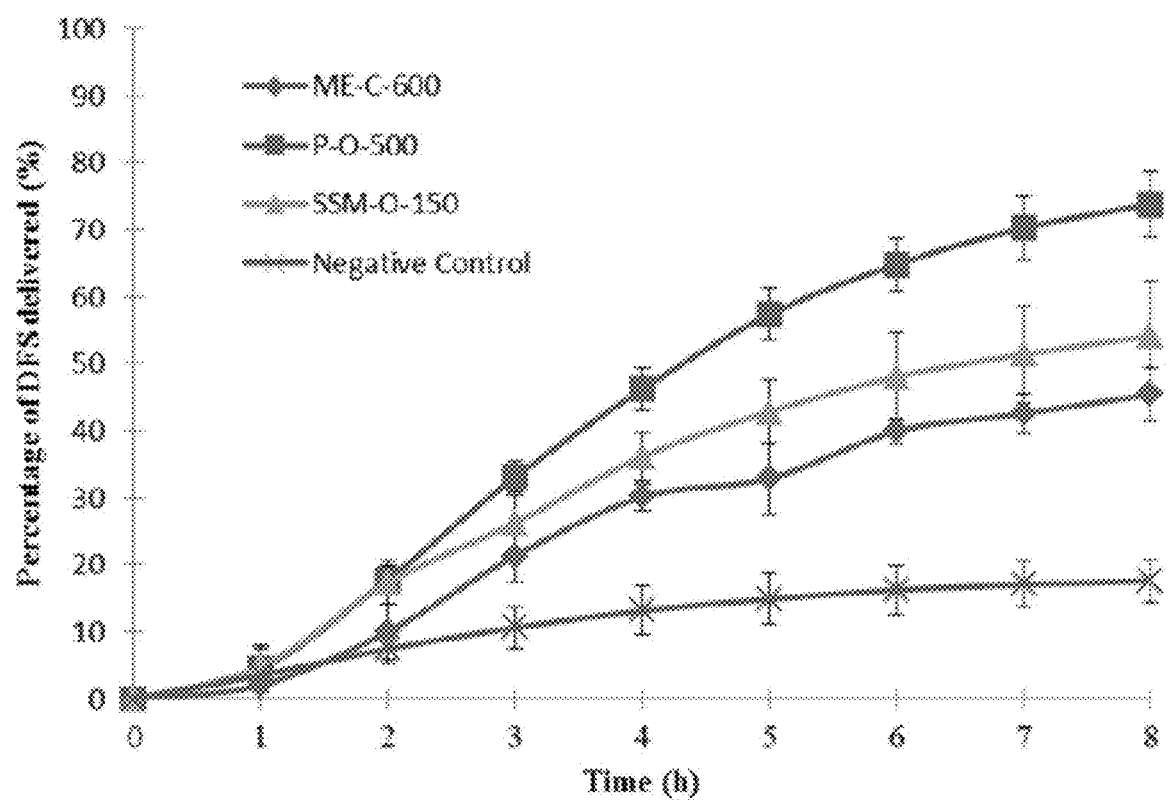
FIG. 16 shows in-vitro study results of DFS delivery with a patch, according to the subject invention, bonded with different types of microneedle plates, active infusion featured.

The validation of diverse drug delivery by a patch of the subject invention was tested by choosing an alternative drug. DFS, a common analgesic, was chosen as a model drug. Quantification of DFS in samples was done by analysis under ultra-performance liquid chromatography (UPLC). With a gradient method A:B=70%:30% to 10%: 90% in 4 min (A=0.02% trifluoroacetic acid (TFA) in $H_2O$; B=0.02% TFA in acetonitrile (ACN)), flow rate=0.45 mL/min with detection wavelength=210 nm. All the data presented was collected from a patch having a 2-layer coated hydrogel, as described in Example 6. FIG. 16 presents a graph of DFS delivery by active infusion transdermal microneedle patch with different types of microneedle plates. DFS exerts low bioavailability in transdermal application because of the presence of stratum corneum in the outermost skin. Negative control is achieved by direct pipetting of a known amount of drug on skin for diffusion. As expected, the amount of DFS transferred is relatively low. Percentage of DFS delivered (17.6±3.2%) after 8 hour testing is also comparable with the result provided by Varghese's group, in which during a 6 hour test, the cumulative dose of DFS by sole diffusion was from 11.1% to 17.9% depending on concentration. (Varghese et al., 1996). The delivery of DFS by zeolite microneedle plate adhered to the patch improves delivery rates, due to the modified dimensions and geometry of the microneedles. Plastic microneedles adhered to the patch yield the highest DFS delivery with about 73.8±4.9% of drug delivered in 8 hour test. The delivery is linear with 97% confidence level ($R^2$=0.9704).

Figure 15:
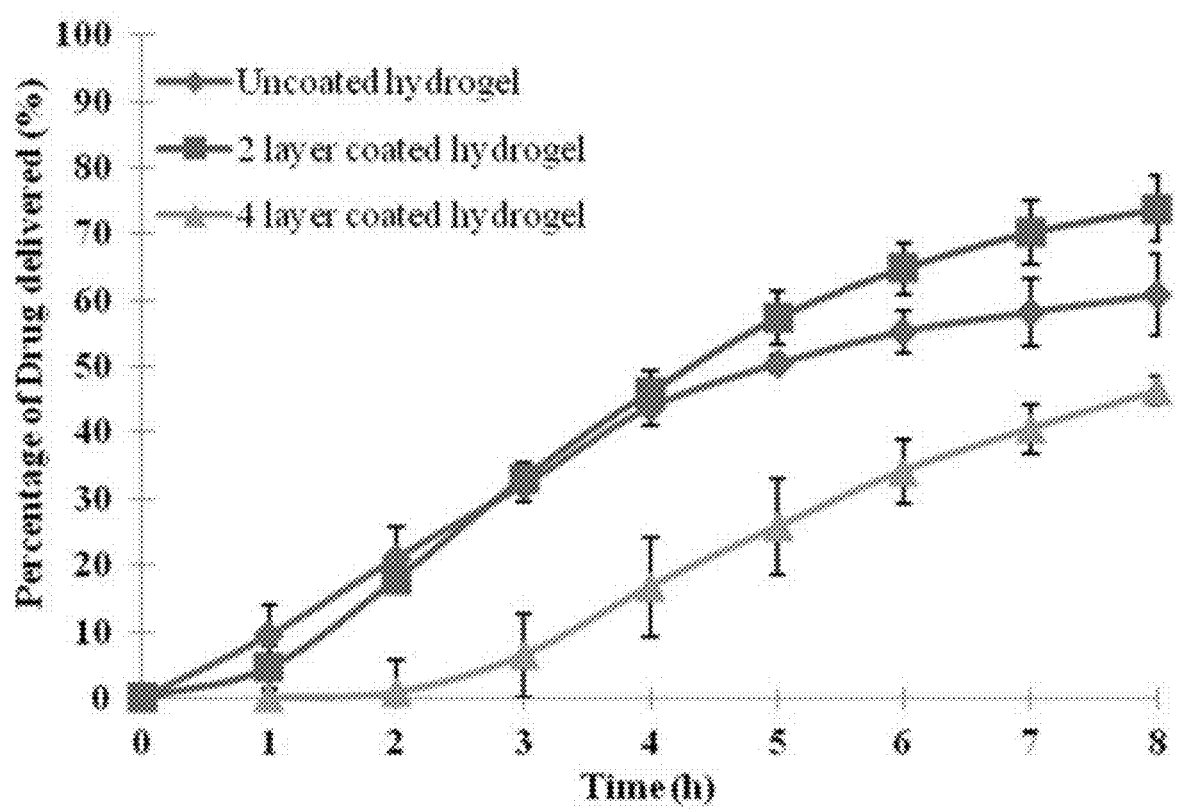
FIG. 15 shows in-vitro study results of the effect of a number of hydrogel PDMS coatings on drug delivery efficiency.

Example 10: In-Vitro Study Using NSAID Drug Diclofenac Sodium (DFS) Using Coated Hydrogels FIG. 15 presents a graph showing the effects of a number of spray-coatings on hydrogel towards the drug (i.e., DFS) delivery efficiency in-vitro. A plastic microneedle plate was used in this experiment. As shown in FIG. 15, the delivery by an adhered plastic microneedle plate with uncoated hydrogel rises exponentially at the initial stage, and starts to level off after 4 hour of testing. In contrast, the DFS delivery with a hydrogel having 2 layers of sprayed-coating hydrogel is impeded initially, but swelled up later. After 8 hours of testing, the amount of drug delivered by a patch with a 2 layer spray-coated hydrogel is higher. The presence of water resistance coating provides a crucial factor for zero order hydrogel swelling in a relatively small swelling ratio condition. Total amount of drug is 60.9±6.1% for uncoated hydrogel and 73.8±4.9% for 2 layered coated hydrogel.

Example 11: In-Vitro Study Using Insulin Drug

Figure 17:
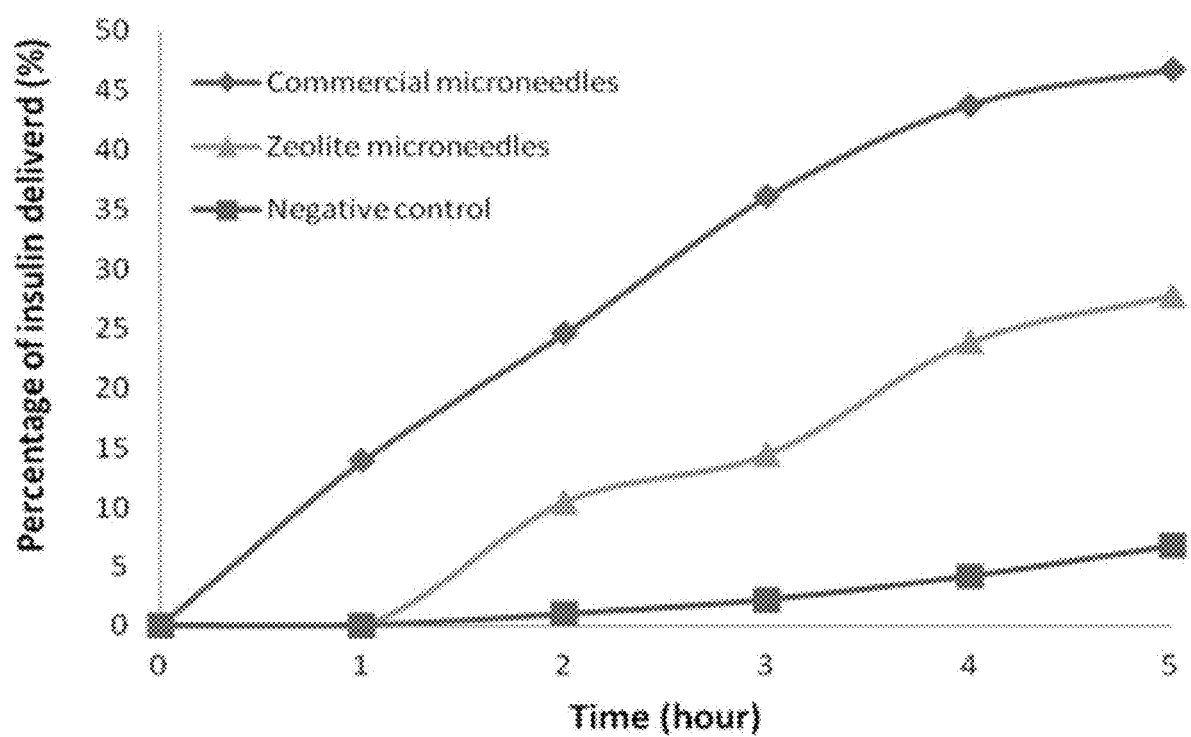
FIG. 17 shows results of an in-vitro study of insulin delivery by an active infusion transdermal microneedle patch, according to the subject invention.

FIG. 17 presents the results of an in-vitro study of insulin delivery by active infusion transdermal microneedle patches using zeolite and commercial microneedles. 70 μL of 4.5 mg/mL insulin stock was stored in the active infusion transdermal microneedle patches. The figure shows that less than 5% of insulin permeated across the non-porated pig skin in the skin patch test (negative control), understood to be due to insulin being a too bulky molecule for passive transdermal delivery. FIG. 17 shows that a linear insulin delivery rate is obtained from both active infusion transdermal microneedle patch with zeolite and commercial microneedles. The longer commercial microneedles had a faster delivery rate than the shorter zeolite microneedle.

Example 12: In-Vivo Study Using NSAID Drug Diclofenac Sodium (DFS)

Figure 18:
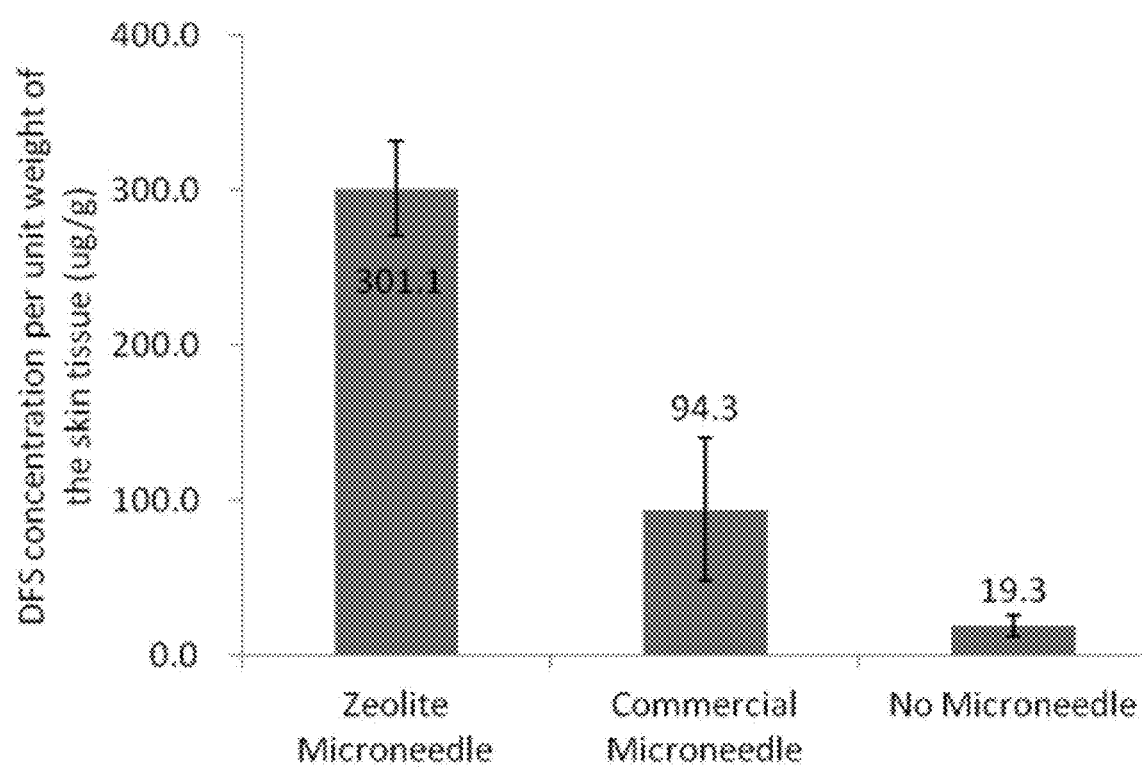
FIG. 18 shows results of an in-vivo study for DFS delivery across skin by zeolite and a commercial microneedle plate.

A in-vivo test was conducted on Sprague Dawley rates between approximately 230 g-250 g to analyze DFS delivery. The rats were anesthetized by a ketamine/xylazine cocktail, and then the abdominal hairs were completely removed by a hair clipper following by chemical depilatory creams. 200 µl of 5 mg/ml DFS in phosphate buffered saline (PBS) was injected through rats' naked skin with either zeolite microneedles or commercial microneedles in bolus. A negative control consisted of placing excess DFS solution on rats' naked skin. After 5 min, the skins were washed by iced DI water. About 1 mm diameter of skin samples at the injection sites were carefully cut and then weighed in 2 ml centrifuge tubes. Then the skin samples were homogenized in 5 fold PBS buffer by sonication. DFS was extracted from the homogenate by liquid-phase extraction using 500 µl ethyl-acetate for twice. The ethyl-acetate was collected into 1.5 ml centrifuge tubes and then removed under vacuum. The residues were reconstituted by 500 µl ACN:$H_2O$ (50:50 w/w ratio) and 200 µl of the reconstituted solution was send for UPLC analysis. FIG. 18 shows a graph of the results of in-vivo DFS delivery across the skin by the different microneedles plates. The transdermal DFS delivery by the commercial microneedle patches showed a nearly 5 times increase when compared with the negative control. While the zeolite microneedle could further have more than 3-fold increase in term of the delivery amount than the commercial microneedle, indicating that although the commercial microneedles were longer, the zeolite microneedles demonstrated better effectiveness for delivery of the DFS across the outermost layer of the skin.

Example 13: In-Vivo Study Using Insulin Drug

An in vivo test of insulin delivery was conducted on Sprague Dawley rats weighing between approximately 230 g-250 g, which were fasting overnight, but free to access water one day before the test. The rats were anesthetized by a ketamine/xylazine cocktail, and the abdominal hairs were completely removed by a hair clipper followed by chemical depilatory creams. About 80 µl of 100 IU/ml human insulin solution was transdermal administrated to individual rats by either zeolite microneedles or the same type of commercial microneedles used in Example 12. Fixed dosed 0.1 IU insulin solution or saline was also subcutaneously injected by syringes to simulate the positive and negative control respectively. The rats' blood glucose levels were recorded by a portable glucose meter (Roche, Accu-Chek Performa Nano) for 6 hours at different time intervals. For the first 4 hours 200 µl of blood samples were also collected by squeezing the rats' tails. The blood samples were centrifuge at 13000 G for 3 min and then the blood plasma was pipetted into 1.5 ml centrifuge tubes and stored under −80° C. for blood insulin test. The blood insulin levels were tested by an ELISA kit (Mercodia, Human Insulin ELISA). Some samples were followed with a 5 fold dilution using the blank calibrator provided by the kit in order to prevent exceeding the calibration limit.

Figure 19:
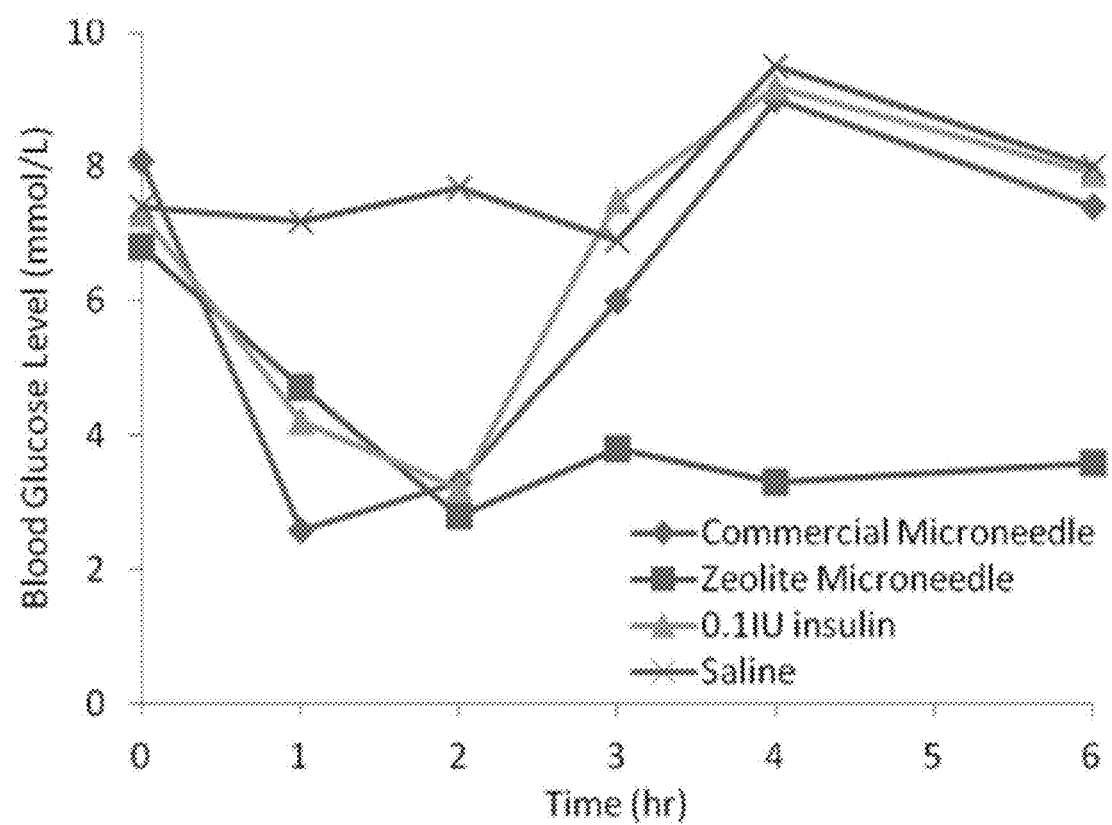
FIG. 19 shows the in-vivo study results of the pharmaceutical effect for the administration of an insulin solution by zeolite and a commercial microneedle plate.

FIG. 19 shows a graph of the pharmaceutical effect of the administration of the insulin solution by different microneedle patches. For all zeolite microneedle, commercial microneedle, and the positive control, a significant pharmaceutical effect could be observed after 1 hour, when the blood glucose level of the rats dropped by about 4-fold from the original level and was subsequently maintained for some hours.

Figure 20:
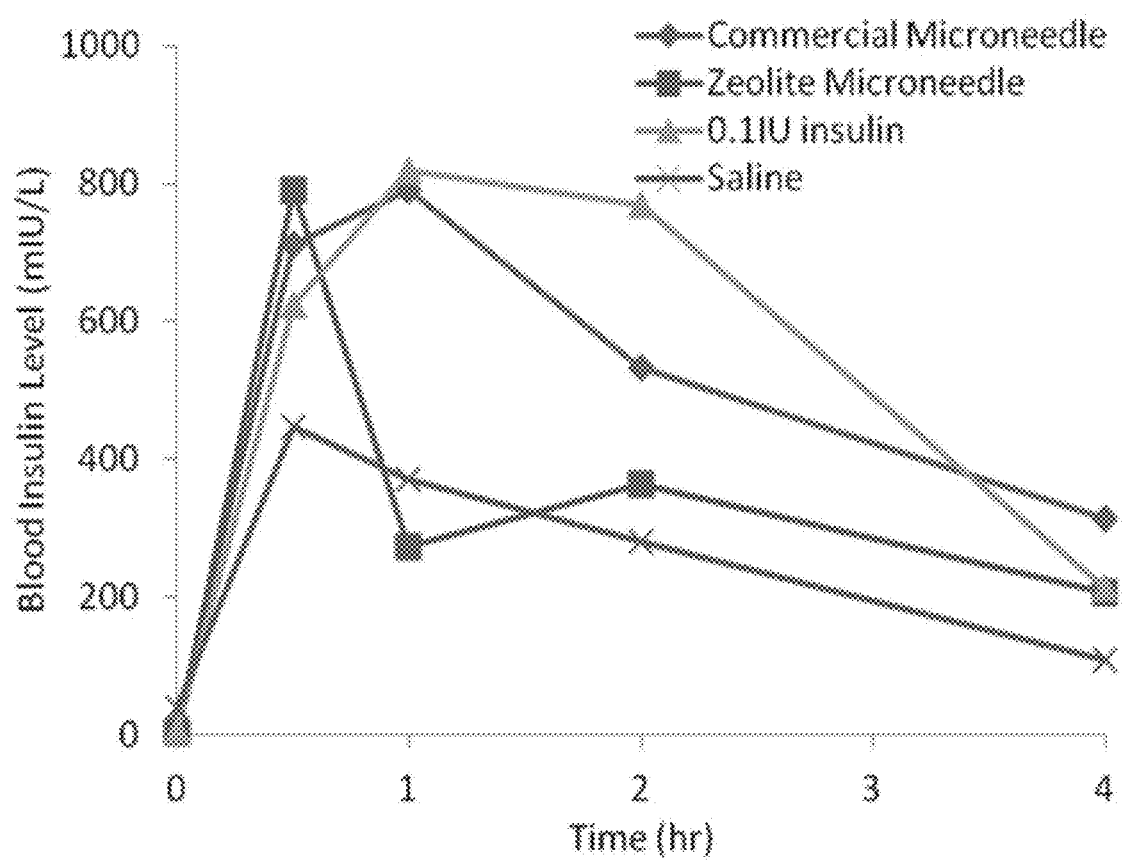
FIG. 20 shows the in-vivo study results of the blood insulin level for rats that were administered an insulin solution by zeolite and a commercial microneedle plate.

FIG. 20 shows a graph of the blood insulin level of the rats used for this in-vivo test. The result was consistent with the observed pharmaceutical effect, as indicated by the $C_{max}$ being the highest and $T_{max}$ being the fastest for the rat that received insulin administration by the transdermal patch. In pharmacokinetics, the administration efficiency of a certain drug is commonly evaluated by its $C_{max}$ and $T_{max}$. $C_{max}$ represents the maximum plasma concentration of the drug and $T_{max}$ represents the time after administration of a drug when the maximum plasma concentration is reached which the rate of absorption equals the rate of elimination.

Example 14: Wearable Transdermal Device

FIGS. 21A and 21B a wearable patch housing design drawing (FIG. 21A) and a prototype of a wearable transdermal patch with belt (FIG. 21B). FIG. 21A show this embodiment with dimensions of the housing to be 31 mm in diameter and 4.87 mm in height. The photograph of the prototype shows the transdermal patch housed within the cavity so that could be worn on the body and the limbs for securing the patch in close contact with the skin.

REFERENCE CITED

US Patent Document

2007/0225676 A1, Prausnitz et al.
2009/0099502 A1, Tokumoto et al.
2009/0030365 A1, Tokumoto et al.
2011/0288485 A1, Tokumoto et al.
U.S. Pat. No. 8,162,901 Gonnelli et al.
U.S. Pat. No. 8,197,435 Prausnitz et al.
U.S. Pat. No. 8,062,835 Tomono
U.S. Pat. No. 8,043,250 Xu
U.S. Pat. No. 8,150,505 Herndon
U.S. Pat. No. 7,798,987 Trautman et al.
U.S. Pat. No. 3,964,482 Gerstel et al.
U.S. Pat. No. 7,332,339 Canham
U.S. Pat. No. 6,844,213 Sparks
U.S. Pat. No. 5,312,456 Reed et al
U.S. Pat. No. 7,588,552 Yeshurun et al.
U.S. Pat. No. 8,137,736 Zhu et al.
2011/0237925 Yue, Ruifeng et al.
U.S. Pat. No. 7,097,776 Govinda Raju
U.S. Pat. No. 7,497,980 Xu et al
U.S. Pat. No. 6,334,856 Allen et al.
U.S. Pat. No. 6,924,087 Yeshurun et al.
U.S. Pat. No. 6,451,240 Sherman et al.
2006/0055090 Lee; Seung-seob et al.
U.S. Pat. No. 7,699,819 Yeung et al.

OTHER PUBLICATIONS

M. R. Prausnitz, S. Mitragotri and R. Langer, "Current status and future potential of transdermal drug delivery". Nature Reviews Drug Discovery, 3 (2004) p. 115-124.
L. Plapied, N. Duhem, A. D. Rieux and V. Preat, "Fate of polymeric nanocarriers of oral drug delivery". Current Opinion in Colloid & Interface Science, 16 (2011) p. 228-237.
R. D. Gorden and T. A. Peterson, "Four myths about transdermal drug delivery". Drug Delivery Technology, 3 (2003) p. 1-7.
S. Srodin, "Transdermal Drug Delivery—Innovations in Technologies Are Opening Market Opportunities". Website article (http://ezinearticles.com/?Transdermal-Drug-Delivery--Innovations-in-Technologies-Are-Opening-Market-Opportunities&id=660128), Jul. 24 2007.
K. A. Stockwell, D. J. Virley, M. Perren, M. M. Iravani, K. J. Jackson, S. Rose and R. Jenner, "Continuous delivery of ropinrole reverses motor deficits without dyskinesia induction in MPTP-treated common marmosets". Experimental Neurology, 211 (2008) p.172-179.

P. A. Sloan, D. E. Moulin and H. Hays, "A clinical evaluation of transdermal therapeutic system fentanyl for the treatment of cancer pain". Journal of Pain and Symptom Management, 16 (1998) p. 102-111.

L. G. Hemkens, U. Grouven, R. Bender, C. Gunster, S. Gutschmidt, G. W. Selke and P. T. Sawicki, "Risk of malignancies in patients with diabetes treated with human insulin or analogues: A cohort study". Diabetologia, 52 (2009) p. 1732-1744.

G. M. Glenn and R. T. Kenney, "Mass vaccination: Solutions in the skin". The Annuals of Pharmacotherapy, 40 (2006) p. 2178-2186.

M. R. Prausnitz and R. Langer, "Transdermal drug delivery". Nature Biotechnology, 26 (2008) p. 1261-1268.

R. K. Sivamani, B. Stoeber, G. C. Wu, H. Zhai, D. Liepmann, and H. Maibach, "Clinical microneedle injection of methyl nicotinate: Stratum corneum penetration". Skin Research and Technology, 11 (2005) p. 152-156.

D. V. McAllister, P. M. Wang, S. P. Davis, J. H. Park, P. J. Canatella, M. G. Allen and M. R. Prausnitz, "Microfabricated needles for transdermal delivery of macromolecules and nanoparticles: Fabrication methods and transport studies". Proceedings of the National Academy of Sciences of the United States of America, 100 (2003) p. 13755-13760.

N. Roxhed, B. Samel, L. Nordquist, P. Griss and G. Stemme, "Painless drug delivery through microneedle-based transdermal patches featuring active infusion". IEEE Transactions on Biomedical Engineering, 55 (2008) p. 1063-1071.

A. Richter, C. Klenke and K. F. Arndt, "Adjustable low dynamic pumps based on hydrogels". Macromolecular Symposia, 210 (2004) p. 377-384.

K. Deligkaris, T. S. Tadele, W. Olthuis and A. van der Berg, "Hydrogel-based devices for biomedical applications". Sensors and Actuators B: Chemical, 147 (2010) p. 765-774.

J. T. Zhang, T. F. Keller, R. Bhat, B. Garipcan and K. D. Jandt, "A novel two-level microstructured poly(N-isopropylacrylamide) hydrogel for controlled release". Acta Biomaterialia, 6 (2010) p. 3890-3898.

A. Kumar, S. S. Lahiri and H. Singh, "Development of PEGDMA: MAA based hydrogel microparticles for oral insulin delivery". International Journal of Pharmaceutics, 323 (2006) p. 117-124.

J. X. Gu, F. Xia, Y. Wu, X. Z. Qu, Z. Z. Yang and L. Jiang, "Programmable delivery of hydrophilic drug using dually responsive hydrogel cages". Journal of Controlled Release, 117 (2007) p. 396-402.

K. L. Yung, Y. Xu, C. Kang, H. Liu, K. F. Lam, S. M. Ko, F. Y Kwan, Thomas M. H. Lee, "Sharp tipped plastic hollow microneedle array by microinjection moulding". Journal of Micromechanics and Microengineering (2012) p. 015016.

T. Caykara, M. Bulut, N. Dilsiz and Y. Akyiüz, "Marcoporous poly(acrylamide) hydrogels: swelling and shrinking behaviors". Journal of Macromolecular Science, Part A: Pure and Applied Chemistry, 43 (2006) p. 889-897.

Y. C. Ah, J. K. Choi, Y. K. Choi, H. M. Ki and J. H. Bae, "A novel transdermal patch incorporating meloxicam: In vitro and in vivo characterization". International Journal of Pharmaceutics, 385 (2010) p. 12-19.

G. Yan, K. S. Warner, J. Zhang, S. Sharma and B. K. Gale, "Evaluation needle length and density of microneedle arrays in the pretreatment of skin for transdermal drug delivery". International Journal of Pharmaceutics, 391 (2010) p. 7-12.

E. Varghese and R. K. Khar, "Enhanced skin permeation of diclofenac by iontophoresis: in vitro and in vivo studies". Journal of Controlled Release, 38 (1996) p. 21-27.

What is claimed is:

1. A transdermal patch device comprising:
   a body piece having a proximal side and a distal side;
   an activator compartment within the body piece;
   an actuator compartment within the body piece and operably connected with the activator compartment through an activator access;
   a drug reservoir at the proximal side of the body piece, a distal side of the drug reservoir adjacent a proximal side of the actuator compartment; and
   a turnable cover in direct contact with the activator compartment and the actuator compartment,
   wherein the activator compartment is configured to surround the actuator compartment such that the activator compartment is not overlapped with the actuator compartment at the proximal side of the body piece in a vertical direction perpendicular to a bottom surface of the body piece,
   wherein, in an initial or pre-activated state, an actuator within the actuator compartment is isolated from an activator in the activator compartment,
   wherein, upon initiation by a user, the activator transits through the activator access into the actuator compartment and contacts the actuator, causing the actuator to swell, whereby the actuator expands in a proximal direction and thereby transmits force to the distal side of the drug reservoir, whereby a drug in the drug reservoir is forced out of the device,
   wherein the activator access opens directly into the activator compartment and directly into the actuator compartment,
   wherein a bottom surface of the activator compartment, the activator access, and a bottom surface of the actuator compartment are disposed on a same imaginary plane that is parallel to the bottom surface of the body piece in such a manner that the activator flows directly from the activator compartment to the actuator compartment through the activator access in a direction parallel to the bottom surface of the body piece, and
   wherein the actuator is a hydrogel.

2. A transdermal patch device according to claim 1, wherein the activator compartment is connected to an injector port of the body piece.

3. A transdermal patch device according to claim 1, further comprising:
   an opening in the body piece;
   an insert in operable communication with a proximal side of the turnable cover, where the activator compartment and the actuator compartment are formed of the insert; and
   at least one trigger mechanism on the turnable cover by which a user can initiate open connection between the actuator compartment and the activator compartment, and
   wherein the turnable cover has a distal side accessible through the opening in the body piece.

4. A transdermal patch device according to claim 3, further comprising at least one breakable gate on the insert.

5. A transdermal patch device according to claim 4, wherein the trigger mechanism is a break trigger that opens the at least one breakable gate when the turnable cover is rotated, whereby open connection is initiated between the actuator compartment and the activator compartment.

6. A transdermal patch device according to claim 3, further comprising at least one slot within the actuator compartment.

7. A transdermal patch device according to claim 6, wherein the trigger mechanism is a switchable gate on the turnable cover that opens and closes the slot when the turnable cover is rotated, whereby open connection is initiated between the actuator compartment and the activator compartment.

8. A transdermal patch device according to claim 3, wherein the turnable cover further comprises a lock accessible through the opening in the body piece.

9. A transdermal patch device according to claim 8, further comprising a key for removably engaging with the lock to rotate the turnable cover.

10. A transdermal patch device according to claim 1, further comprising a body piece overlay in which the drug reservoir is disposed.

11. A transdermal patch device according to claim 10, further comprising a drug port operably connected to the drug reservoir in the body piece overlay.

12. A transdermal patch device according to claim 11, wherein the drug port is sealable.

13. A transdermal patch device according to claim 10, further comprising at least one arm on the insert and at least one block on the body piece overlay, wherein the block engages with the arm to inhibit the insert from being rotated.

14. A transdermal patch device according to claim 10, further comprising a membrane between the actuator compartment and the drug reservoir.

15. A transdermal patch device according to claim 10, further comprising a microneedle disposed on a proximal side of the drug reservoir.

16. A transdermal patch device according to claim 15, wherein the microneedle comprises plastic, metal, ceramic, silicon, glass, or zeolite.

17. A transdermal patch device according to claim 13, further comprising one or more fasteners on at least one of the body piece, the body piece overlay, or the insert.

18. A transdermal patch device according to claim 3, further comprising a coating that forms a seal between two or more adjacent components within the transdermal patch.

19. A transdermal patch device according to claim 18, wherein the coating comprises a silicon-based material.

* * * * *